United States Patent
Gerginov

(10) Patent No.: US 11,555,873 B2
(45) Date of Patent: Jan. 17, 2023

(54) SYSTEMS AND METHODS FOR INCREASING THE DEGREE OF ATOMIC POLARIZATION IN OPTICALLY PUMPED MAGNETOMETERS BASED ON MAGNETIC FIELD ZEROING

(71) Applicant: The Regents of the University of Colorado, a body corporate, Denver, CO (US)

(72) Inventor: Vladislav Gerginov, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 130 days.

(21) Appl. No.: 17/166,594

(22) Filed: Feb. 3, 2021

(65) Prior Publication Data

US 2022/0091200 A1 Mar. 24, 2022

Related U.S. Application Data

(60) Provisional application No. 62/969,272, filed on Feb. 3, 2020.

(51) Int. Cl.
*G01R 33/26* (2006.01)
*G01R 33/032* (2006.01)
*G01R 33/00* (2006.01)
*A61B 5/245* (2021.01)

(52) U.S. Cl.
CPC ............ *G01R 33/26* (2013.01); *A61B 5/245* (2021.01); *G01R 33/0017* (2013.01); *G01R 33/032* (2013.01)

(58) Field of Classification Search
CPC .. G01R 33/26; G01R 33/0017; G01R 33/032; A61B 5/245
See application file for complete search history.

(56) References Cited

U.S. PATENT DOCUMENTS

2020/0292639 A1* 9/2020 Le Prado ............... G01R 33/24

OTHER PUBLICATIONS

Bell, William E. et al., "Optically Driven Spin Precession," Physical Review Letters, vol. 6, No. 6, pp. 280-281, Mar. 15, 1961.
FieldLine Inc., "Home," https://web.archive.org/web/20210122211023/http://fieldlineinc.com/, 4 pages, Jan. 22, 2021.
Geometries, "Products," https://www.geometrics.com/, 6 pages, 2018.
(Continued)

*Primary Examiner* — Susan S Lee

(57) ABSTRACT

The disclosure describes optically pumped magnetometers and systems incorporating, and methods of operating, the same. An optically pumped magnetometer according to one embodiment of the present technology includes a vapor cell configured to contain an atomic absorber such as rubidium-87, and at least one light source in optical communication with the vapor cell. The optically pumped magnetometer includes components positioned and configured to provide a bias field, and induce a zeroing field, within the vapor cell. Among other useful and advantageous ends, embodiments of the present technology provide for increasing the degree of atomic polarization in optically pumped magnetometers based on zeroing the bias magnetic field during the optical pumping process.

20 Claims, 23 Drawing Sheets

(56) References Cited

OTHER PUBLICATIONS

Gerginov, Vladislav et al., "Pulsed Operation Of A Miniature Scalar Optically Pumped Magnetometer," Journal of the Optical Society of America B, vol. 34, No. 7, pp. 1429-1434, Jul. 2017.

Gerginov, Vladislav et al., "Scalar Magnetometry Below 100 fT/Hz1/2 In A Microfabricated Cell," IEEE Sensors Journal, vol. 20, No. 21, pp. 12684-12690, Nov. 1, 2020.

Grujic, Zoran D. et al., "A Sensitive And Accurate Atomic Magnetometer Based On Free Spin Precession," The European Physical Journal D, vol. 69, No. 135, 10 pages, May 21, 2015.

Hunter, D. et al., "Free-lnduction-Decay Magnetometer Based On A Microfabricated Cs Vapor Cell," Physical Review Applied, vol. 10, pp. 014002-1-014002-10, Jul. 6, 2018.

Hunter, Dominic et al., "Waveform Reconstruction With A Cs Based Free-lnduction-Decay Magnetometer," Optics Express, vol. 26, No. 23, pp. 30523-30531, Nov. 12, 2018.

Jaufenthaler, Aaron et al., "Pulsed Optically Pumped Magnetometers: Addressing Dead Time And Bandwidth For The Unshielded Magnetorelaxometry Of Magnetic Nanoparticles," Sensors, vol. 21, 19 pages, Feb. 9, 2021.

Lucivero, V. G. et al., "A Femtotesla Quantum-Noise-Limited Pulsed Gradiometer At Finite Fields," Quantum Information and Measurement, 2 pages, 2019.

UCLA Engineering, "Internet50: Celebrating The 50th Anniversary Of The Internet On Oct. 29, 2019," https://www.youtube.com/watch?v=oqZmQhhd27o&5=29226s, Minute 8:32:28, 1 page, Oct. 29, 2019.

Wilson, Nathanial et al., "Wide-Bandwidth Atomic Magnetometry Via Instantaneous-Phase Retrieval," Physical Review Search, vol. 2, pp. 013213-1-013213-9, Feb. 26, 2020.

\* cited by examiner

SYSTEMS AND METHODS FOR INCREASING THE DEGREE OF ATOMIC POLARIZATION IN OPTICALLY PUMPED MAGNETOMETERS BASED ON MAGNETIC FIELD ZEROING

CROSS-REFERENCE TO RELATED APPLICATIONS

This application claims priority to U.S. Provisional Application No. 62/969,272 filed Feb. 3, 2020, which is incorporated herein by reference in its entirety for all purposes.

STATEMENT REGARDING FEDERALLY SPONSORED RESEARCH OR DEVELOPMENT

This invention was made with government support under grant number N6523619C8013 awarded by DOD/DARPA, and grant number EB027004 awarded by the National Institutes of Health. The government has certain rights in the invention.

BACKGROUND

Optically pumped magnetometers find scientific applications such as studies of fundamental physics, as well as commercial uses such as magnetic anomaly detection, studies of geomagnetism, nanoparticle detection and relaxometry, nuclear magnetic resonance (NMR), magnetic resonance imaging (MRI) and induction imaging.

Applications requiring ultimate sensitivity performance are in magnetocardiography (MCG) and magnetoencephalography (MEG), where the non-cryogenic and non-invasive nature of optically pumped magnetometers makes them an attractive alternative to other technologies.

The human brain continuously generates brain waves that can be used as an indicator of brain activity, consciousness, medical condition, or the like. It is not uncommon for brain waves to be measured in a controlled environment (e.g., a shielded room in a hospital). One traditional way of detecting brain activity is through the use of electrodes placed on the scalp. The skull acts as an isolator, and the signals that are detected are essentially only from the thin layer close to the scalp. Unfortunately, the electrodes cannot detect signals that originate from deep within the brain. For those signals that originate from deep within the brain, implanted electrodes are needed. Implantation of electrodes within the brain is invasive.

Magnetic field sensors exist that can measure brain activity. However, the typical devices used in medicine (e.g., MEG) are often cryogenic and rely on superconductive sensors. As such, these devices come with the corresponding complexity, expense and maintenance. Additionally, cryogenic devices are typically stationary, restricting the subject's movements, and do not allow flexible arrangement of sensor arrays. Accordingly, systems and methods are needed to provide a reliable, non-invasive solution for measuring deep brain activity.

SUMMARY

Various embodiments of the present technology generally relate to optically pumped magnetometers operating in a nonzero DC (direct current) bias magnetic field. The magnetometer's sensitive element is a vapor cell containing an atomic absorber such as (but not limited to) rubidium-87 ($^{87}$Rb) isotope and a buffer gas such as (but not limited to) nitrogen ($N_2$) preventing the absorber's atomic polarization relaxation through wall collisions. The bias magnetic field adds to the magnetic signal of interest vectorially to a total magnetic field at the magnetometer's sensitive element. The magnitude of the total magnetic field is measured by the optically pumped magnetometer and the magnetic signal of interest is extracted from the measurement. More specifically, some embodiments of the present technology relate to systems and methods for increasing the degree of atomic polarization in optically pumped magnetometers based on zeroing the bias magnetic field during the optical pumping process.

A first aspect of the present technology provides a method for operating an optically pumped magnetometer. The method includes the step of placing an atomic absorber in a bias field within a vapor cell of an optically pumped magnetometer. The atomic absorber contained within the vapor cell during performance of method 2000 may be, or include, rubidium-87 ($^{87}$Rb). Other suitable atomic absorbers may be utilized in the method. The method also includes the step of generating a zeroing field to cancel the bias field within the vapor cell of the optically pumped magnetometer.

The method according to the first aspect of the disclosure can also include the step of activating a pump light source of the optically pumped magnetometer to initiate optical pumping within the vapor cell. The method can further include the step of deactivating the pump light source of the optically pumped magnetometer to finish the optical pumping in the vapor cell. The method may also include the step of disengaging the zeroing field within the vapor cell of the optically pumped magnetometer. The method may further include the step of activating a probe light source of the optically pumped magnetometer. The method can also include the step of measuring the total field within the vapor cell.

In the method according to the first aspect of the disclosure, the step of activating the probe light source may include activating the probe light source during the optical pumping. The method step of generating the zeroing field may include activating zeroing coils to zero the bias field. The method step of generating the zeroing field may include applying the zeroing field in a direction opposite of that of the bias field.

According to the first aspect of the disclosure, the method steps of activating the pump light source and activating the probe light source may include separately activating the pump and probe light sources from a single light source. The step of separately activating the pump and probe light sources from the single light source may include modifying at least one of: an amplitude, a frequency modification, and a modification to a state of polarization, of the single light source.

The method according to the first aspect of the disclosure may include the step of turning off the pump light source using amplitude attenuation, frequency detuning, or by a change in a state of polarization. The method of the first aspect of the disclosure can include the step of detecting probe light polarization to detect the phase evolution of an atomic polarization of the atomic absorber caused by changes in the bias field.

A second aspect of the present technology provides a system. The system includes a vapor cell for containing an atomic absorber. The vapor cell can contain $^{87}$Rb as the atomic absorber. Other suitable atomic absorbers may be utilized in the system. The system includes at least one light source. The at least one light source is configured to: generate and direct a pump light, and a probe light, through the vapor cell. The at least one light source may include at least two light sources including: a first light source to generate the pump light; and a second light source to generate the probe light. The system includes zeroing coils to zero (e.g., by a zeroing field) a bias field within the vapor cell.

The system according to the second aspect of the disclosure can include a detector for measuring a total field within the vapor cell. The system of the second aspect may include means for providing the bias field within the vapor cell. The system according to the second aspect of the present technology can include means for providing the bias field within the vapor cell. The means for providing the bias field may include biasing coils to induce the bias field within the vapor cell.

A third aspect of the present technology provides an optically pumped magnetometer. The optically pumped magnetometer includes a vapor cell configured to contain an atomic absorber. The vapor cell can be configured to contain $^{87}$Rb as the atomic absorber. Other suitable atomic absorbers may be utilized in the optically pumped magnetometer. The optically pumped magnetometer includes at least one light source in optical communication with the vapor cell. The at least one light source can be configured to direct a pump light, and a probe light, into the vapor cell along one or more path(s). The optically pumped magnetometer includes means for providing a bias field within the vapor cell. The optically pumped magnetometer includes means for inducing a zeroing field within the vapor cell. The means for inducing the zeroing field is/are positioned sufficiently relative to the vapor cell to zero the bias field upon the zeroing field being induced in the vapor cell. The optically pumped magnetometer includes a detector positioned in the path of the at least one light source.

The optically pumped magnetometer according to the third aspect of the disclosure can include a controller operatively coupled to at least one of: the at least light source, the means for providing the bias field, the means for inducing the zeroing field, and the detector. The controller may be operatively coupled to the at least one light source, and be configured to control a timing sequence of energizing the at least one light source to alternately provide a pump light, and a probe light, through the vapor cell. The controller may be operatively coupled to the means for inducing the zeroing field, and be configured to control a timing sequence of energizing the means for inducing the zeroing field to alternately enable, and disable, the zeroing field within the vapor cell.

BRIEF DESCRIPTION OF THE DRAWINGS

Embodiments of the present technology will be described and explained through the use of the accompanying drawings.

FIGS. 11A-11C illustrate simplified $^{87}$Rb ground state energy diagram with the stretched states circled (FIG. 11A), optical pumping in zero magnetic field (FIG. 11B), and optical pumping in a finite magnetic field (FIG. 11C) with Larmor precession of the atomic polarization that reduces the degree of atomic polarization created by the light field.

Figure 1A:
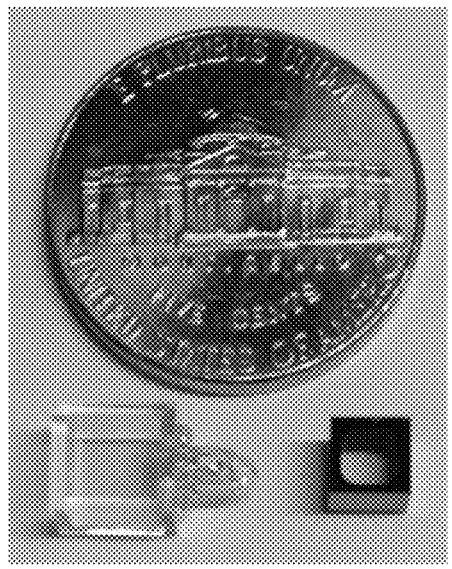
FIG. 1A illustrates an example of vapor cells used in optical pumped magnetometer. Left lower corner—68 mm$^3$ glass-blown cell. Right lower corner—18 mm$^3$ microfabricated vapor cell.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to optically pumped magnetometers. More specifically, some embodiments of the present technology relate to systems and methods for increasing the degree of atomic polarization in optically pumped magnetometers based on magnetic field zeroing. Detecting brain activity in a non-invasive manner with high reliability in a non-specialized environment would be advantageous for a number of reasons. For example, the brain activity could be used to connect a brain to a computer. Tissue and skull are transparent to these magnetic signals and, as such, no insertion is needed to detect signals that originate from deep within the brain.

Optically pumped magnetometers (OPMs) have attracted a lot of attention recently due to their application in MEG. A wearable MEG imager based on OPMs has been considered as one of the ten breakthrough technologies of 2019. Currently, the most sensitive sensors operate in a zero field environment and require heavy shielding in 3D to achieve noise floors approaching 10 $fT/Hz^{1/2}$. Magnetically shielded rooms cost ~$1 M. OPMs for detection of low-frequency magnetic signals can operate in two possible configurations—zero field and total field OPMs. The total field is the vectorial sum of the magnetometer's bias field (e.g., an artificial field or natural field from the Earth) plus the much smaller measured magnetic signal field (e.g., brain signal, etc.).

Zero field OPMs operate in a zero bias magnetic field, measure a given component of the magnetic signal, and require shielding to ensure the bias magnetic field is zero. Total field, or scalar optically pumped atomic magnetometers detect the magnitude of the total field and operate at finite (non-zero) bias magnetic fields, reducing the shielding requirements from 3D to 1D, and opening up the possibility of operation in an unshielded environment. The best performance of a scalar optical magnetometer is achieved when the atomic medium reaches the highest degree of atomic polarization. Higher atomic polarization results in: 1) increased signal amplitude (effective use of the available absorbing atoms); and 2) increased signal coherence time (reduced signal loss with time) due to suppressed spin-exchange atom collision broadening.

A convenient method for driving the resonance in an optically pumped magnetometer is the use of pump light modulation (Bell, W. E. & Bloom, A. L., "Optically driven spin precession", Phys. Rev. Lett., 1961, 6, 280, which is incorporated by reference herein in its entirety for all purposes). The resulting atomic polarization needs to be orthogonal to the bias magnetic field that is measured. Throughout the present disclosure, creating atomic polarization orthogonal to the bias magnetic field by optical pumping, and detecting the corresponding Larmor precession, is discussed. When the pump light modulation is resonant with the atom's Larmor precession frequency, a resonance is excited. A phase detection can then be performed to determine the exact value of the Larmor precession frequency, which is determined by the total magnetic field value. Among the advantages of the all-optical excitation is reduced sensor cross-talk, which is present when an AC (alternating current) magnetic field excitation is used.

Achieving high atomic polarization in ambient (Earth's) magnetic field is difficult when the magnetic resonant excitation is driven by optical pulses. To induce Larmor precession, the optical pumping process must create an atomic polarization orthogonal to the bias magnetic field. In this case, the magnetic field counteracts the build-up of atomic polarization that is created through optical pumping. To achieve high atomic polarization, the optical pulse needs to be very short and very intense, requiring a short pulse duration and a high peak optical power—only delivered by highly specialized lasers and/or fast modulators. Another limit on the achievable atomic polarization is due to the intrinsic speed of the optical pumping process, which involves multiple light absorption and spontaneous emission events.

The free induction decay (FID) method is an alternative method of operation (see, for example, Grujić, Z. D. et al. Eur. Phys. J. D (2015) 69: 135; Hunter, D. et al., Phys. Rev. Appl. 10, 014002, 2018 which is incorporated by reference herein in its entirety for all purposes). Using the FID method, sensitivities have been found at 200 $fT/Hz^{1/2}$ using a 30 mm diameter, 14000 $mm^3$ vapor cell, and 3 $pT/Hz^{1/2}$ using a 1.8 mm diameter, 1.5 mm thickness, 15 $mm^3$ volume microfabricated cell. The advantage of the FID method is simplicity and accuracy since no reference oscillators or prior knowledge of the Larmor precession frequency are needed as in the case of magnetometers based on the Bell-Bloom method. The Larmor precession is detected in the absence of optical pumping, improving the accuracy of the method. The FID method consists of a temporal cycle that includes an optical pumping phase and a detection phase.

To remove the strict pumping light pulse duration and peak power requirements mentioned above, various embodiments of the present technology modify the optical pumping phase of the magnetometer operation cycle. During the optical pumping phase, the bias magnetic field was zeroed using a short magnetic field pulse applied in the direction opposite of that of the bias magnetic field (magnetic field zeroing method). This allowed the optical pumping phase to last longer in various embodiments, thereby allowing the use of longer pulses with reduced peak power, and resulting in a higher degree of atomic polarization compared to the case of pulsed optical pumping in a non-zero magnetic field. Possible sensor cross-talk is limited to the optical pumping phase and does not influence the detection phase. During the second, detection phase of the cycle, when the Larmor precession frequency is measured, the zeroing pulse and the pumping light are off, and the highly stable bias field plus magnetic signal of interest are measured to extract the magnetic signal.

Various embodiments of the present technology increase the degree of atomic polarization in optically-pumped magnetometers that measure the value of the total ambient (Earth's or artificial) magnetic field. The precession rate of the atomic polarization is typically used to measure the value of the total magnetic field, as they are related through the atomic gyromagnetic ratio. Some embodiments increase the duration of atomic polarization preparation, for example, allowing the use of longer duration and/or lower peak power optical pumping pulses, which leads to a higher degree of atomic polarization. The higher degree of atomic polarization results in a higher signal amplitude and longer coherence time, both of which lead to increased magnetometer sensitivity.

Various embodiments of the present technology provide for a wide range of technical effects, advantages, and/or improvements. For example, various embodiments include one or more of the following technical effects, advantages, and/or improvements: 1) techniques for increasing the degree of atomic polarization in optically pumped atomic magnetometers based on magnetic field zeroing; 2) improvements resulting in increased signal amplitude by a factor of 2 compared to the case without magnetic field zeroing; 3) techniques for increased signal coherence time, which is an indication of higher degree of atomic polarization compared to the case without magnetic field zeroing; 4) OPMs with sensitivity of less than 100 fT/Hz$^{1/2}$ in <100 mm$^3$ vapor cells using the Bell-Bloom and the FID methods (record sensitivity for the FID method); 5) techniques for the avoidance of detrimental effect of nonzero magnetic field on the process of atomic polarization preparation accomplished by optical pumping; 6) OPMs with high achievable degree of atomic polarization in ambient (Earth's or artificial) magnetic field, which increases the amplitude and the coherence time of the processing atomic polarization; 7) increased magnetometer bandwidth by the use of instantaneous phase response of the atomic polarization caused by magnetic field change during the FID detection phase; and/or 8) systems with increased amplitude and coherence time of the atomic polarization precession leads to improved sensitivity of the optically pumped magnetometer. Some embodiments include additional technical effects, advantages, and/or improvements to computing systems and components.

In the following description, for the purposes of explanation, numerous specific details are set forth in order to provide a thorough understanding of embodiments of the present technology. It will be apparent, however, to one skilled in the art that embodiments of the present technology may be practiced without some of these specific details.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

Various embodiments of the present technology provide for a magnetometer with 18 mm$^3$ microfabricated vapor cell that has a noise floor of 90 fT/Hz$^{1/2}$ (Bell-Bloom method) and 100 fT/Hz$^{1/2}$ (FID method), respectively. Other embodiments provide for a magnetometer with 68 mm$^3$ glass-blown vapor cell that has a noise floor of 70 fT/Hz$^{1/2}$ for the Bell-Bloom and FID methods, respectively. The vapor cells used for all experiments below are shown in FIG. 1A. In the glass blown cell case, a continuous phase detection (Bell-Bloom scheme) was compared to a pulsed operation (FID scheme). Without field zeroing, the magnetometer sensitivity is twice lower (the noise floor is twice higher) than that of the sensitivities achieved with the Bell-Bloom method, or that of the FID method with field zeroing. The achieved sensitivities below 100 fT/Hz$^{1/2}$ in <100 mm$^3$ vapor cells are of interest in Magnetoencephalography (MEG) applications.

Figure 1B:
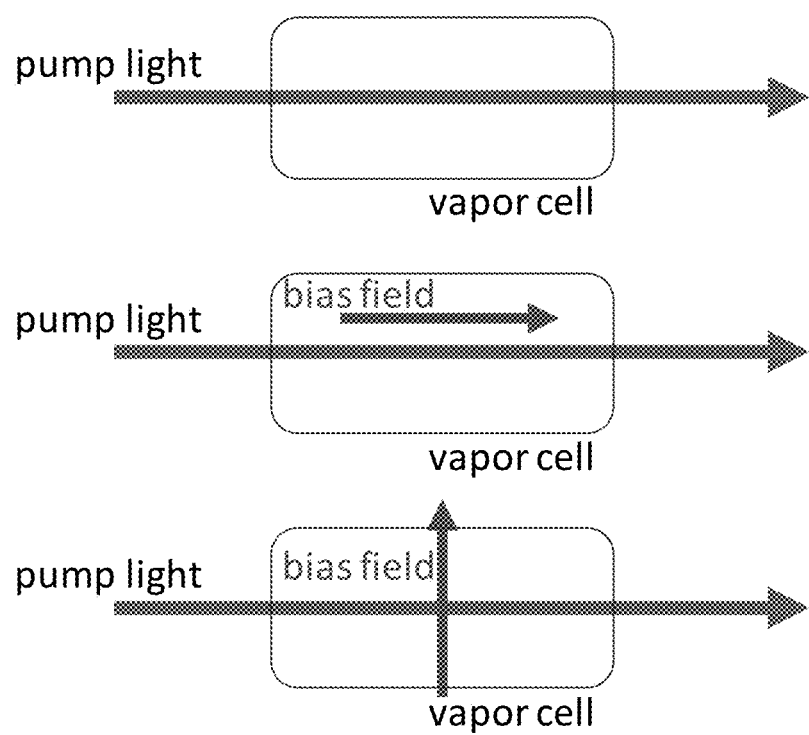
FIG. 1B is a visual illustration of the optical pumping and magnetic fields of an optical pumped magnetometer.

FIG. 1B is a visual illustration of the optical pumping and magnetic fields of an optical pumped magnetometer. In the top figure, there is a zero bias field. As such, the light determines the optically-pumped final atomic state, and maximum optical pumping efficiency is reached. In the middle figure, the bias field is parallel to the pump light. As a result, the light and the field determine the same optically-pumped final atomic state. While there is maximum optical pumping efficiency, the magnetic field strength (zero sensitivity) cannot be measured because there is no atomic polarization orthogonal to the bias field. The bottom figure illustrates a bias field orthogonal to the pump light. In this situation, the bias field counteracts the optical pumping. The magnetic field distributes the atoms from the state prepared by the optical pumping to other atomic states, leading to temporal evolution of these atomic states called Larmor precession, and thereby reduces the optical pumping efficiency. However, this configuration allows for measurement of the magnetic field strength. The bias magnetic field causes Larmor precession, with the precession frequency proportional to the bias field through the atomic gyromagnetic ratio.

The increase of optical pumping efficiency has two positive effects. First, the degree of atomic polarization (or atomic state preparation) is increased (higher portion of the atoms are prepared in the same state). The result is stronger signal. Second, the increased degree of atomic polarization (or atomic state preparation) with more atoms in the same state leads to increased relaxation time or reduced decoherence. This is a result of the reduction of the spin-exchange relaxation, which is caused by atom-atom collisions. The increased relaxation time allows for longer detection phase, and higher signal to noise (SNR).

Finally, the use of field zeroing allows for controlling the duration of the optical pumping phase. Without zeroing, the optical pumping duration is determined by the bias field value (and the corresponding Larmor frequency) and requires very fast modulation rates of an intense light source. The duration of the optical pumping pulse—through AM, FM or PM modulation of the pumping light—can be much longer than the Larmor precession period set by the measured bias field. This allows to use slower modulation rates and less intense light sources.

Figure 2A:
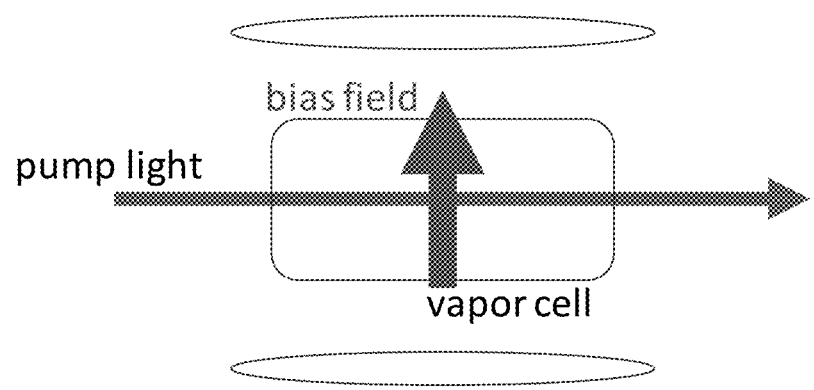
FIG. 2A illustrates a conventional method of optical pumping.

FIG. 2A illustrates a conventional method of optical pumping. As illustrated in FIG. 2A, source bias field coils generate a bias field across the vapor cell. The source could also be Earth's field, or a permanent magnet. The magnetometer then measures the bias field (not shown) where the bias field variation is the signal of interest. The total field is the magnitude of the "bias field" (e.g., Earth's) plus the magnetic field of interest (e.g., brain signal) that is being measured added vectorially.

Figure 2B:
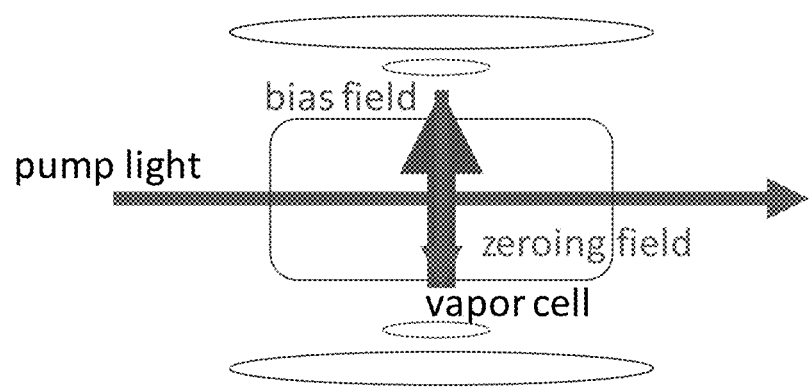
FIG. 2B illustrates an example of a field zeroing method for operating an optical pumped magnetometer.

FIG. 2B illustrates an example of a field zeroing method for operating an optical pumped magnetometer. In accordance with various embodiments, the zeroing field coils are introduced to temporarily null the bias field (e.g., during the optical pumping phase). The coils can then be turned off during the detection phase, and the bias field is measured during that phase (not shown). Again, the bias field variation is the signal of interest. It might be possible to turn off the bias field itself if it is artificially created, and to avoid the use of the extra zeroing coils. Typically, the artificially created bias field must be very low noise, which is not necessarily compatible with the required high-speed switching to implement field zeroing.

Figure 3:
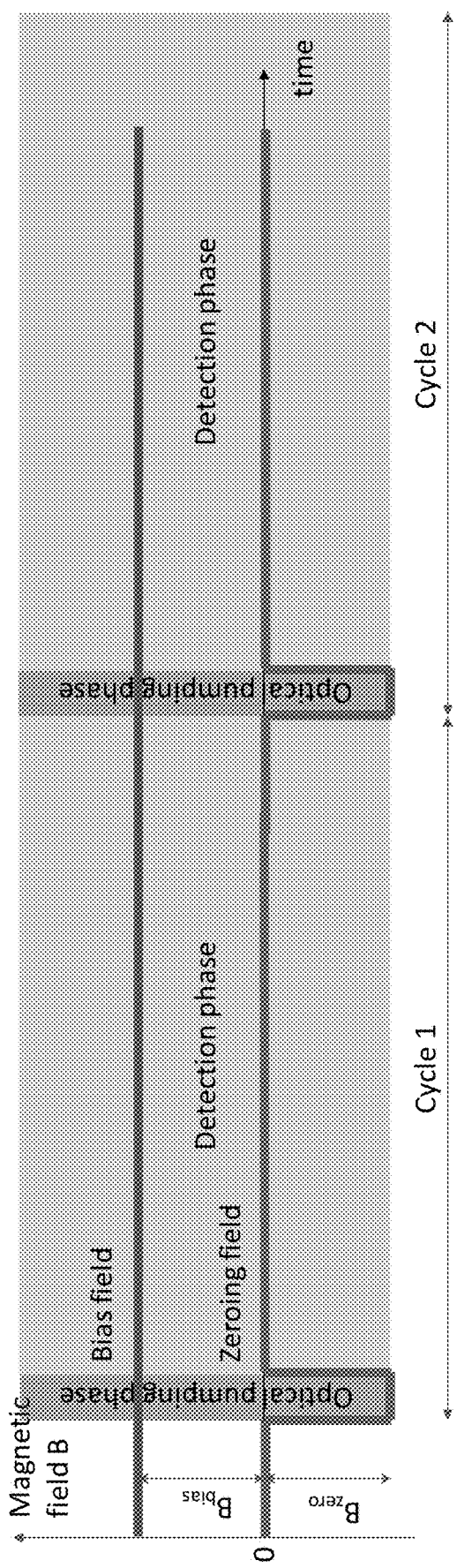
FIG. 3 is a plot illustrating an example of the temporal implementation of some embodiments of the field zeroing method.

FIG. 3 is a plot illustrating an example of the temporal implementation of some embodiments of the field zeroing method. As illustrated in FIG. 3, during the pump phase, $B_{bias}+B_{zero}=0$. During the detection phase, there is no optical pumping (pump light is off), and $B_{zero}=0$.

Figure 4A:
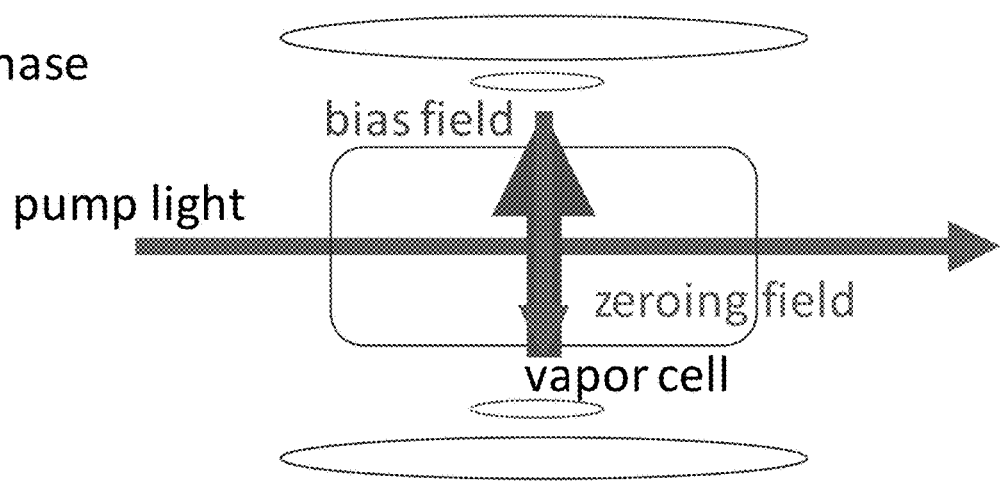
FIGS. 4A and 4B illustrate an example of the pump phase and the probe phase of a high-bandwidth magnetic field detection.
Figure 4B:
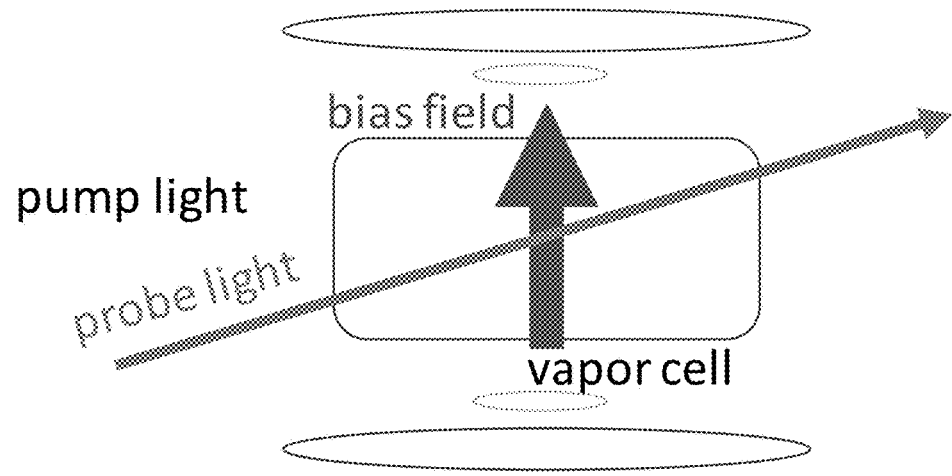

FIGS. 4A-4B illustrate an example of the pump phase and the probe phase, respectively, of a high-bandwidth magnetic field detection. During the pump phase, the preparation time of the atomic polarization is determined by the process of optical pumping. During the probe, or detection, phase, the precession of the already prepared atomic polarization instantaneously changes in the bias magnetic field. During the detection phase, the pump light is off, and no optical pumping takes place.

Figure 5:
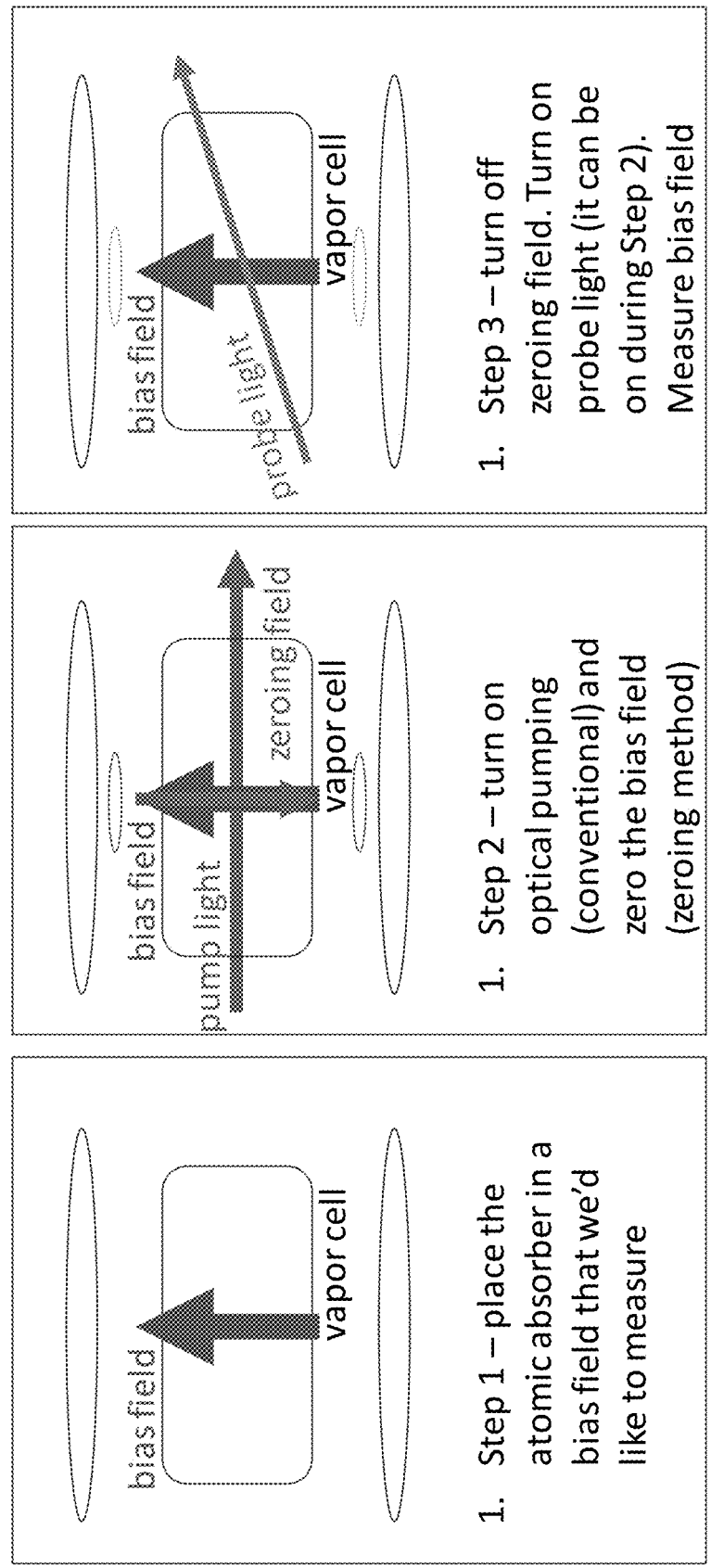
FIG. 5 illustrates an example of a free induction decay (FID) magnetometer operation as modified by various embodiments of the present technology.

FIG. 5 illustrates an example of a process of FID magnetometer operation as modified by various embodiments of the present technology. At step 1, the atomic absorber is placed in the bias field that will be measured. At step 2, optical pumping is turned on and the bias field is zeroed. In accordance with various embodiments, step 2 can be modified compared to the conventional method. In some embodiments, the physical modification is the added zeroing coils, or another mechanism to zero the bias field shortly (e.g., modulation, switching, etc.). The turning off of the pump light can be accomplished by amplitude attenuation, frequency detuning, or by a change in the state of its polarization. The probe light can be different from the pump light, or can be pump light with modified frequency or state of polarization. At step 3, the zeroing field is turned off, the probe light is turned on, and the bias field is measured. In some embodiments, the probe light is turned on during step 2.

Figure 6:
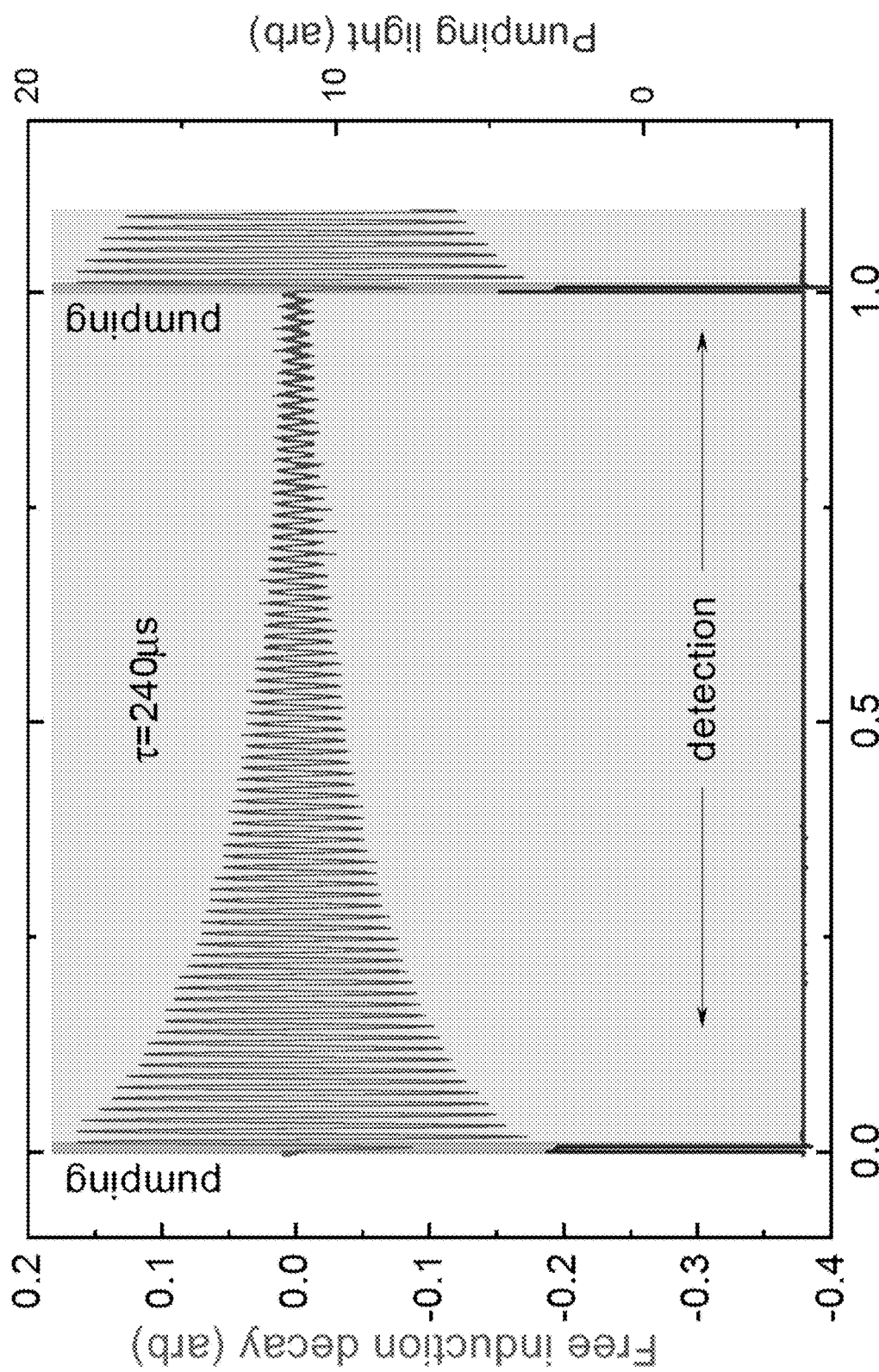
FIG. 6 shows an example of an FID cycle with field zeroing off, with an FID signal decay time constant of ~240 µs with an 18 mm$^3$ microfabricated cell.
Figure 7:
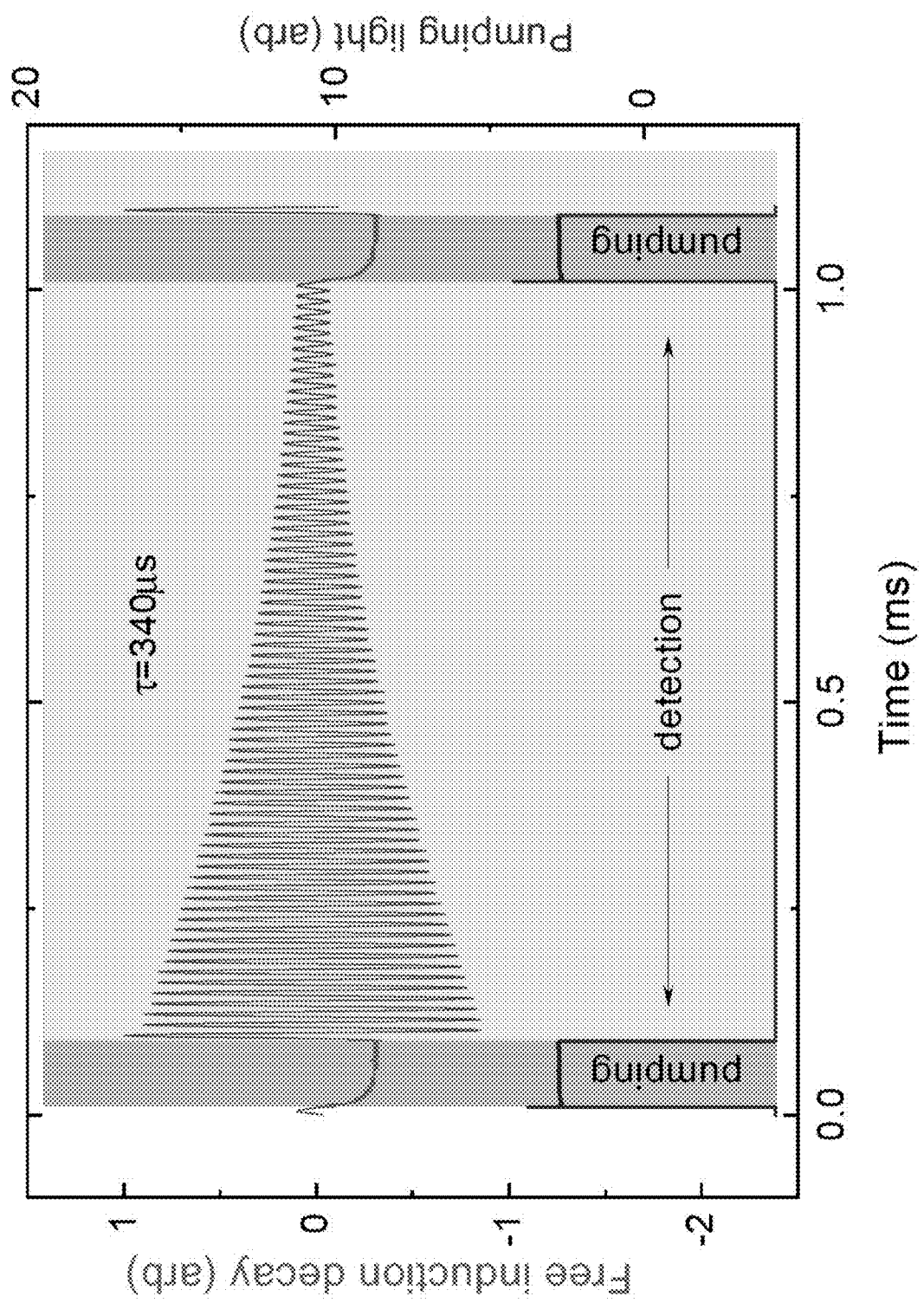
FIG. 7 shows an example of the FID cycle with field zeroing on, with an FID signal decay time constant of ~340 µs with the 18 mm$^3$ microfabricated cell.
Figure 8:
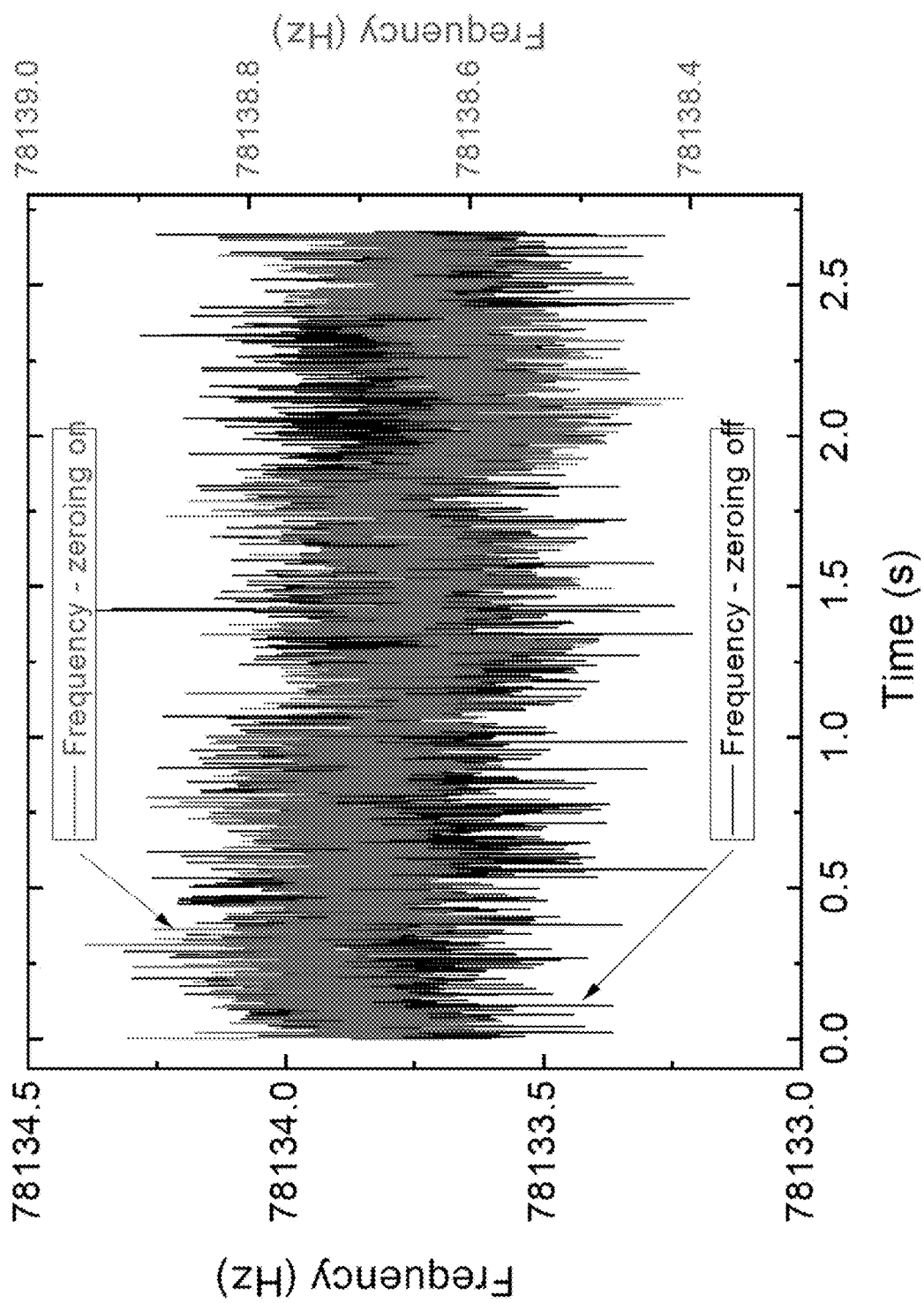
FIG. 8 shows an example of the measured precession frequency of an FID magnetometer recorded every 1 ms with and without field zeroing with the 18 mm$^3$ microfabricated cell.
Figure 9:
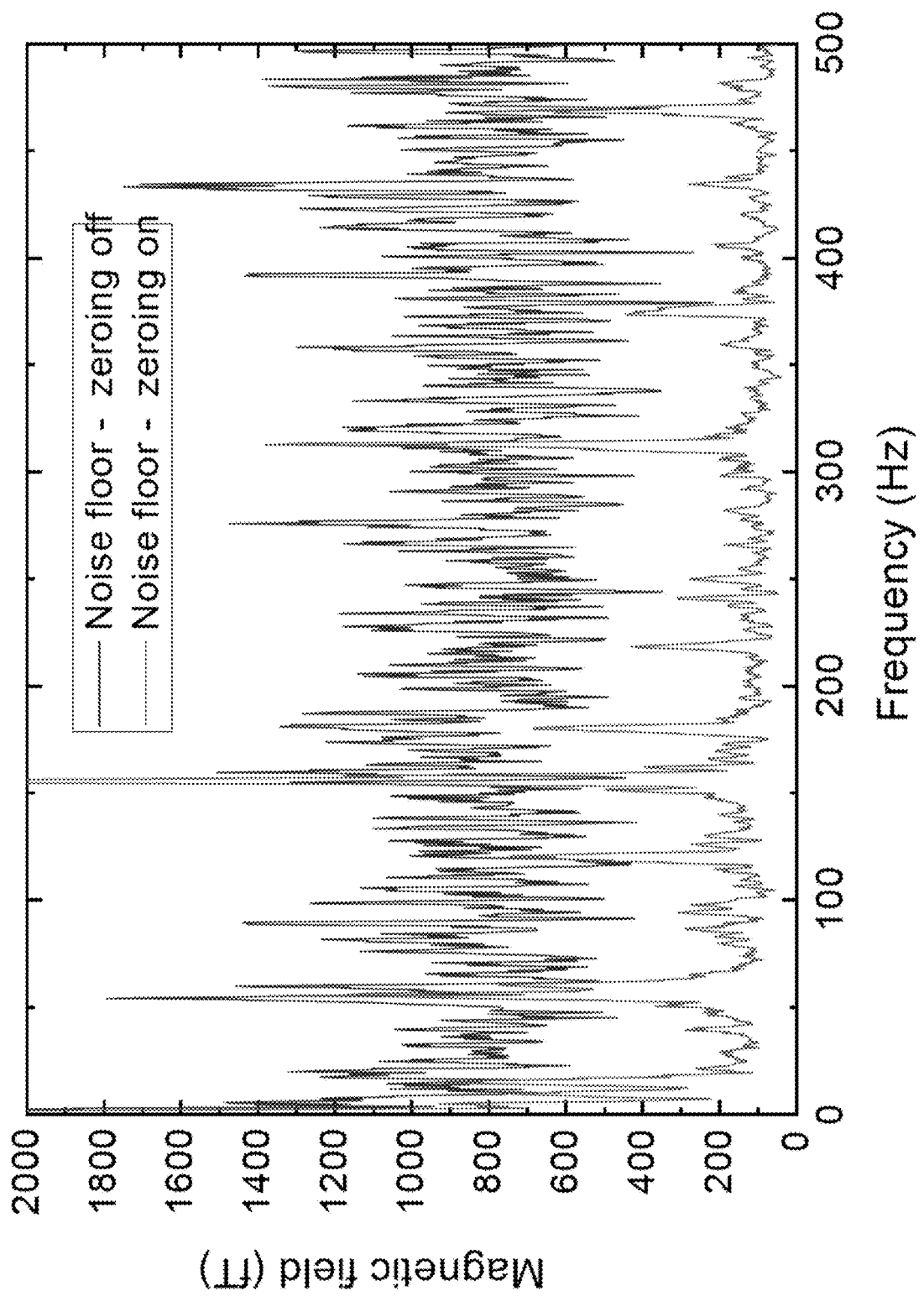
FIG. 9 shows an example of the FID magnetometer noise spectrum with and without field zeroing with the 18 mm$^3$ microfabricated cell.

FIG. 6 shows an example of the FID cycle with field zeroing off. FIG. 7 shows an example of the FID cycle with field zeroing on. FIG. 8, shows an example of the FID-frequency response with the field zeroing off and on. FIG. 9 shows an example of the FID spectrum noise floor.

Figure 10:
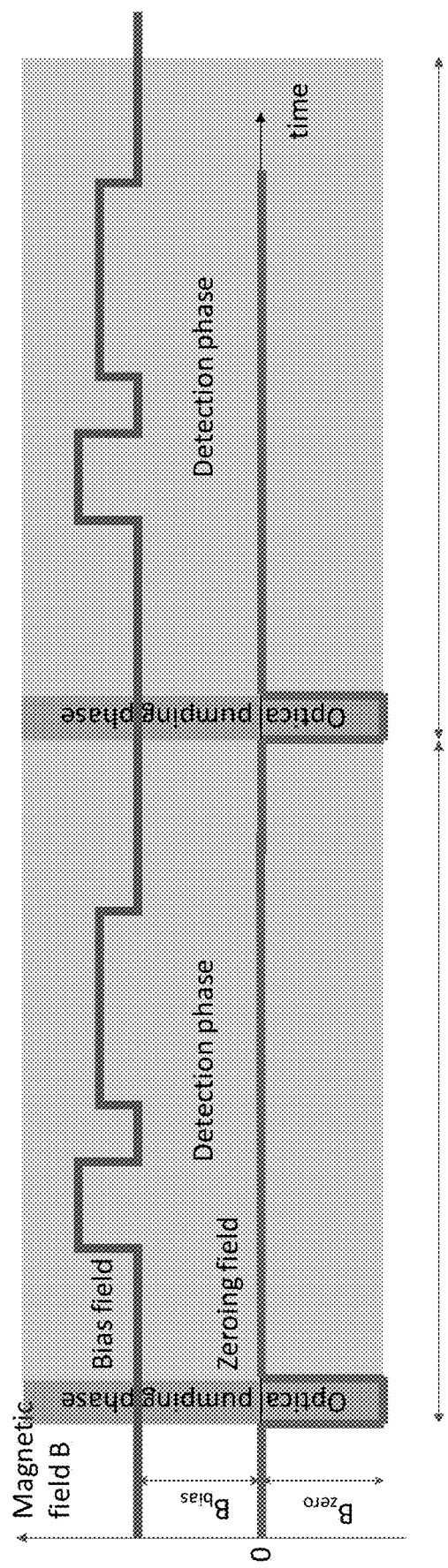
FIG. 10 is a plot illustrating an example of the increased bandwidth of an FID magnetometer with the 18 mm$^3$ microfabricated cell.
Figure 1:
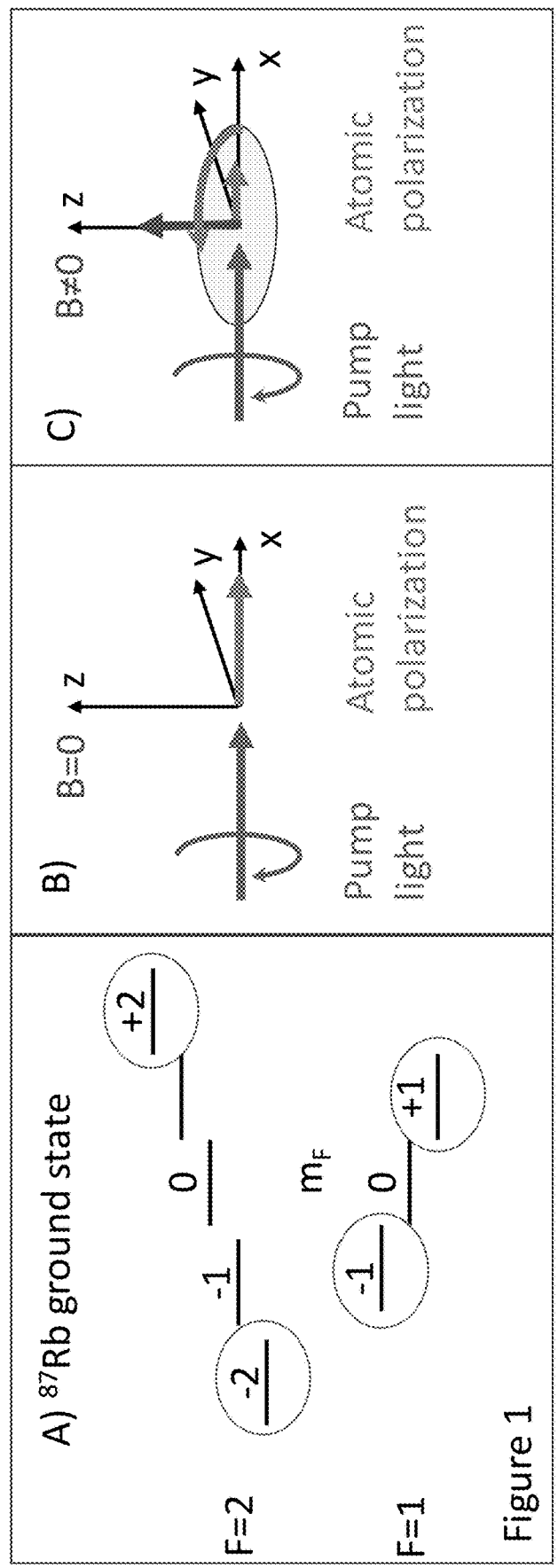

FIG. 10 is a plot illustrating an example of the increased bandwidth of an FID magnetometer. During the FID detection phase, the atomic polarization temporal evolution follows the bias field evolution without phase lag. This means that the bandwidth of the bias field measurement is not limited by the time constant of the optical pumping process or the relaxation time of the atomic polarization. The use of probe light polarization rotation allows for detection of the phase evolution of the atomic polarization, and also to follow phase changes of the atomic polarization caused by stepwise change in the bias field.

Because of the limited duration of the detection phase (determined by the relaxation time of the atomic polarization), the sensitivity of the bias field measurement is limited. For repeated processes (the bias field change repeats in time in a cycling fashion) one can use cycle averaging to increase the measurement sensitivity without compromising the bandwidth of the single-shot measurement. FIG. 10 shows two such cycles.

Examples

Various embodiments of the present technology also provide a high-bandwidth operation of the magnetometer in the FID scheme, which may be applied in areas such as magneto relaxometry (detection of magnetic nanoparticles) as well as ultralow field NMR (ULF-NMR). The high-bandwidth operation may be used with boxcar averaging to recover the intrinsic magnetometer sensitivity. The boxcar averaging operation is also compatible with the field zeroing method, which allows increased signal amplitude.

The sensitivity of optically pumped scalar magnetometers can be increased by preparing the majority of atoms in a stretched state (total angular momentum projection mF=±F)—see for example FIG. 11A which a shows simplified $^{87}$Rb ground state energy diagram. The atoms can be prepared in any of the stretched states (circled) by using optical pumping with circularly-polarized light.

When the atoms are exposed to zero bias magnetic field, the stretched states are eigenstates of the light polarization. When the atoms are transferred to these states, the sample has a maximum atomic polarization oriented along (or against) the helicity axis of the light's circular polarization (oriented along the x-axis, as shown in FIG. 11B). In the high-buffer gas vapor cell ($^{87}$Rb+700 Torr $N_2$) used in one example embodiment, the right circular polarization pump beam prepared the F=2, $m_F$=+2 stretched state.

The best measurement configuration for a total field magnetometer is achieved when the atomic polarization is oriented in a plane orthogonal to the direction of the bias magnetic field (oriented along the z-axis, as shown in FIG. 11C). The magnetic field eigenstates are different from these of the light. In the eigenstates basis of the magnetic field, the atomic states experience a phase evolution, with the result that due to the nonzero field, the orientation of the atomic angular momentum (or atomic polarization) precesses around the field axis (in the xy plane of FIG. 11C). This represents a Larmor precession around the field direction. The presence of the magnetic field transverse to the optical pumping direction removes atoms from the optically prepared stretched state (the atomic polarization is no longer aligned with the direction of circular polarization), counteracting the effect of optical pumping. In the continuous regime, with both light and bias field on, the effective atomic polarization is distributed uniformly in the xy plane (a steady state, no resonance).

Bell-Bloom magnetometers are a class of optically-pumped atomic magnetometers where atomic precession resonance is induced by modulation of pump light properties (optically-driven spin precession). The use of optical modulation results in a reduced sensor cross-talk compared to magnetometers where the excitation is done with time-varying magnetic fields. In some Bell-Bloom magnetometers, the atomic polarization precession is excited by amplitude modulation of the pump light every precession period (or once per multiple precession periods). The precession rate of the atomic polarization is proportional to the applied magnetic field through the atomic gyromagnetic ratio and is used to deduce the value of the bias magnetic field and its changes by using its effect on a probe light field.

For short, strong optical pumping pulses, most of the atoms are in a stretched state oriented along the light's polarization direction during the pulse, and precess freely the rest of the Larmor period (Free Induction Decay). The requirement for high atomic polarization is to have the optical pumping pulse much shorter than the Larmor period —otherwise a steady state will be approached, with broader resonance of reduced amplitude.

In Earth's magnetic field of 50 µT, the atomic precession of $^{87}$Rb atoms in F=2 ground state has a Larmor frequency of 50 µT×7 kHz/µT=350 kHz, or a period of 2.86 µs. A pumping pulse duration lasting 1% of the Larmor period is then 29 ns long. This is a very short time to perform effective optical pumping that requires multiple light absorption/ spontaneous emission events for each atom. The short pumping time requires significant light power to be concentrated in the optical pumping pulse, but more importantly, the optical pumping pulse duration approaches the speed of the optical pumping process, which requires each atom to participate in multiple cycles of optical photon absorption and spontaneous emission. As a result, one cannot reach a high atomic polarization within a short optical pumping time, and the resulting precession signal has a small amplitude. Also, since not all the atoms are transferred to the stretched state, the spin-exchange resonance broadening additionally broadens the resonance. One could reach higher atomic polarization by a series of weak, short pulses repeating at the Larmor precession frequency, which requires a knowledge of the Larmor precession frequency and a tight timing control of the pulsed pump light source.

These two effects reduce the magnetometer's measurement sensitivity. So far, the best sensitivity results have been achieved with multiple pumping pulses of <1 us duration from a several-watt peak-power pulsed laser system, with pulse repetition rate synchronized with the Larmor precession frequency. Such short pulses are difficult to achieve with continuous laser systems, and specialized high-power pulsed lasers need to be developed. Also, the pulse repetition rate needs to match the Larmor precession frequency, which depends on the bias field.

Figure 12:
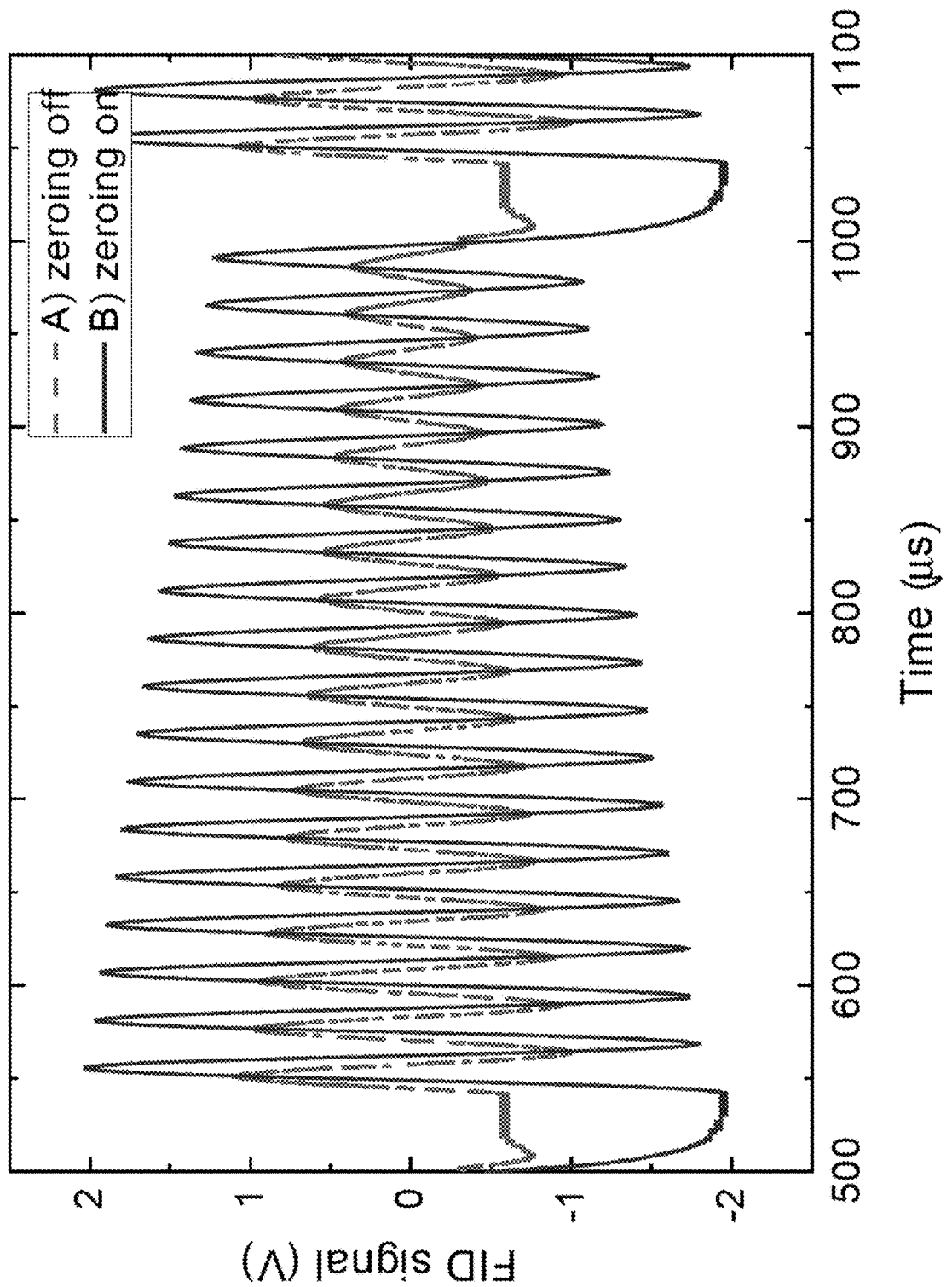
FIG. 12 illustrates an example of an FID signal amplitude as a function of time without field zeroing during the pumping phase (dashed line) and with field zeroing during the pumping phase (solid line) with the 18 mm$^3$ microfabricated cell.

In FIG. 12, the dashed curve shows the free induction decay signal at 73 kHz atomic polarization precession frequency with optical pumping performed in a finite bias magnetic field. The long optical pump pulse does not result in high atomic polarization as the non-zero magnetic field reduces the achieved atomic polarization. The optical pumping without field zeroing is optimal for shorter pump duration (see, e.g., solid line trace).

Field Zeroing Method

An experimental sequence was implemented that separated the optical pumping and atomic polarization phases of the measurement cycle. During the optical pumping process, the bias magnetic field was turned to zero by applying a magnetic field pulse with magnitude equal to that of the bias magnetic field, and with direction opposite to that of the bias magnetic field. As shown in FIG. 11B, since there is no atomic polarization precession, the optical pumping is very effective and can last as long as the bias magnetic field is kept zero or the decoherence process limits it. If the magnetic field is not perfectly zeroed during the optical pumping phase, the optimal duration of the optical pumping phase is shorter than the zero field case, but can still be significantly longer than the optimal duration in ambient (Earth's) magnetic field that is limited by the period of Larmor precession. Also, in a multiple cycle regime, the extracted Larmor frequency of one cycle can be used to determine the zeroing field magnitude for the next cycle, thus allowing the magnetometer in field zeroing mode to follow large changes in the bias field that do not exceed significantly the repetition rate of the cycle (typically 1 kHz).

Since the duration of the optical pumping with field zeroing can be much longer, the pump light power requirements are not that severe. In the field zeroing regime according to the present technology, less peak optical power is required, and effective optical pumping into the stretched state can be achieved with a medium-power amplitude-modulated lasers or microsecond-pulse amplitude modulators rather than a high-power nanosecond pulsed lasers.

Once maximum atomic polarization is achieved, the magnetic field pulse and the pump light are turned off to perform a measurement of the total magnetic field. The atoms are now exposed to the magnetic field to be measured, and the atomic polarization precesses freely. The Free Induction Decay signal of the atomic polarization with field zeroing is shown in FIG. 12, solid line. The signal amplitude is a factor of 2 higher than the achieved amplitude without magnetic field zeroing (FIG. 12, dashed line), which has been optimized in terms of optical pumping pulse duration.

Figure 13:
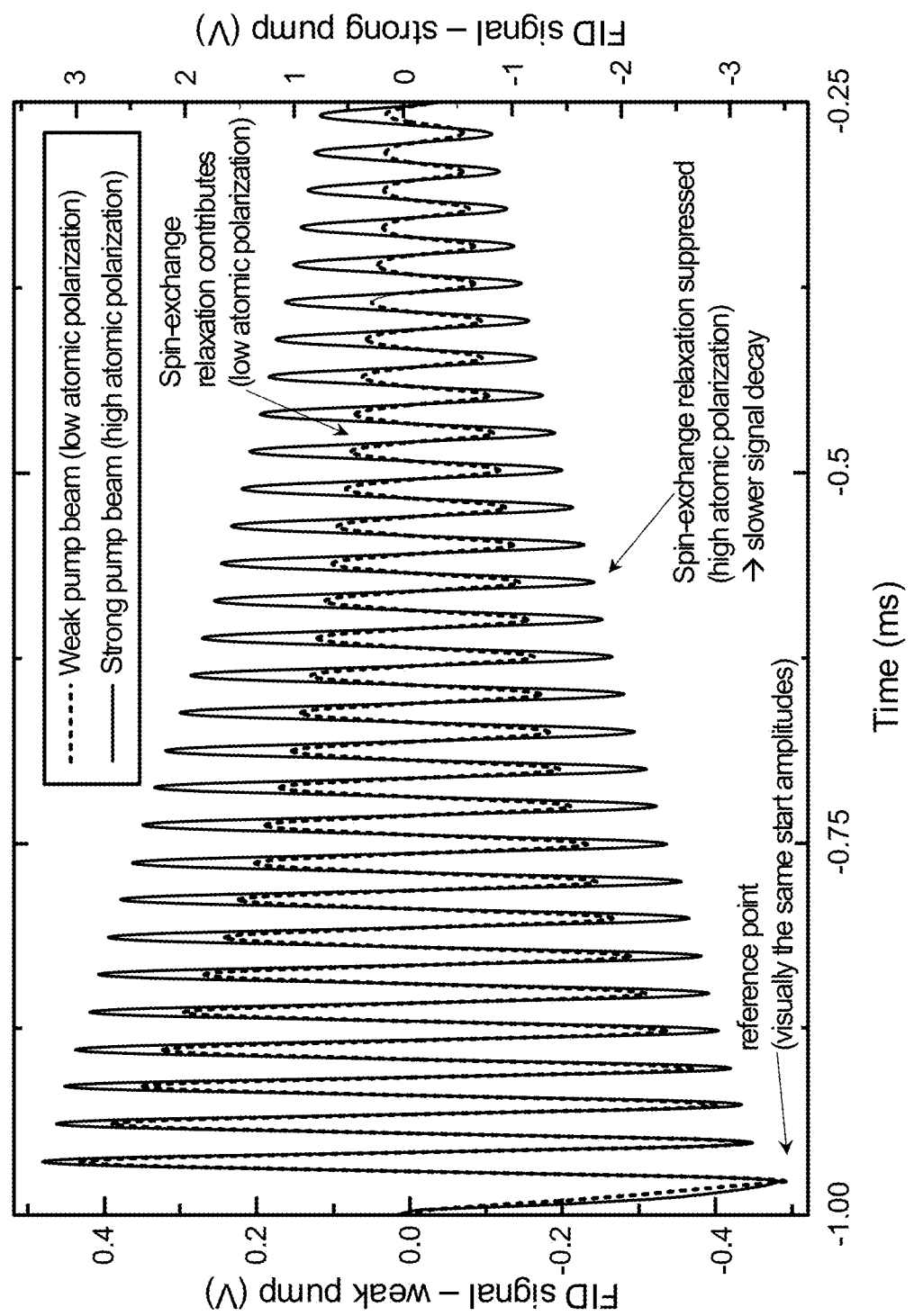
FIG. 13 illustrates an example of an FID signal amplitude as a function of time without field zeroing during the pumping phase and with field zeroing during the pumping phase with the 18 mm$^3$ microfabricated cell according to one or more embodiments of the present technology. The right scale shows the duration of optical pumping pulse. The FID signal with field zeroing has increased coherence time (slower signal decay rate).

FIG. 13 illustrates the effect of high atomic polarization on the signal decay time (decoherence time). If the optical pumping power is low, the achieved atomic polarization (left scale) is a factor of ~10 lower. The signal decay is exponential and contains a contribution from spin-exchange relaxation through atom collisions. The spin-exchange relaxation is an indication that a significant fraction of the atoms is not prepared in the stretched atomic state. With high optical pumping power (right scale) the atomic polarization signal decay is slower and has a non-exponential character, indicating that a high degree of atomic polarization is achieved, and that the spin-exchange relaxation is suppressed at the beginning of the FID signal. This is an indication that a significant portion of the atoms is in the stretched state, and that the majority of atoms contribute to the signal. The effective result is a narrower resonance with higher amplitude—both resulting in an improved magnetometer sensitivity.

Sensitivity (Noise Floor) of the Bell-Bloom and FID Magnetometers

Figure 14:
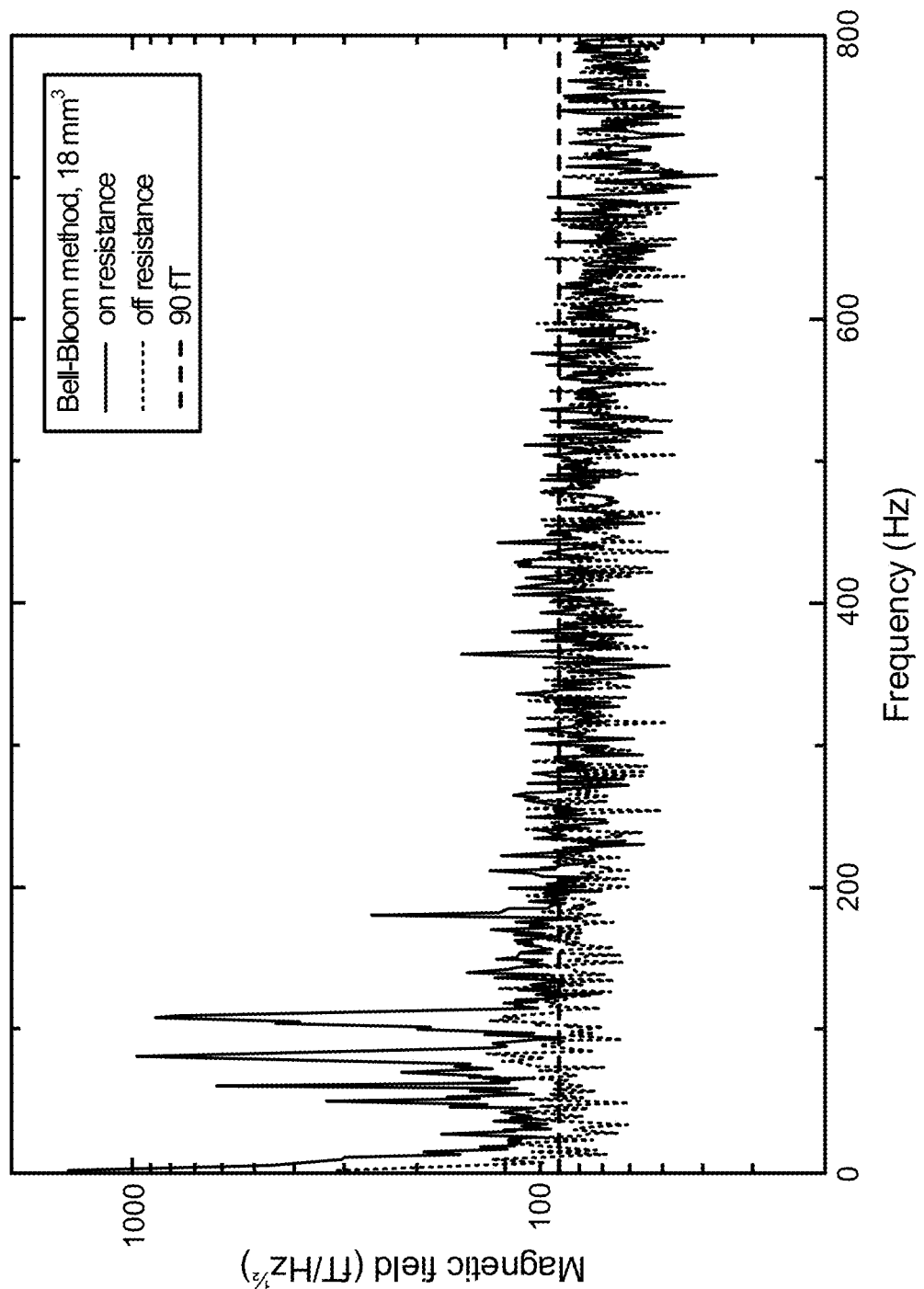
FIG. 14 illustrates an example of the sensitivity of the 18 mm$^3$ microfabricated vapor cell magnetometer with 100 fT/Hz$^{1/2}$ noise floor level using the Bell-Bloom method. The on-resonance line shows the magnetic field noise spectrum with pronounced peaks at low frequencies, and the off-resonant line shows the noise floor of the magnetometer.

FIG. 14 demonstrates the sub-100 $fT/Hz^{1/2}$ noise floor of the 18 $mm^3$ microfabricated vapor cell using the Bell-Bloom method. The setup is identical to the one shown in Gerginov, V.; Krzyzewski, S. & Knappe, S., "Pulsed operation of a miniature scalar optically pumped magnetometer", J. Opt. Soc. Am. B, OSA, 2017, 34, 1429-1434, which is hereby incorporated by reference herein in its entirety for all purposes.

Figure 15:
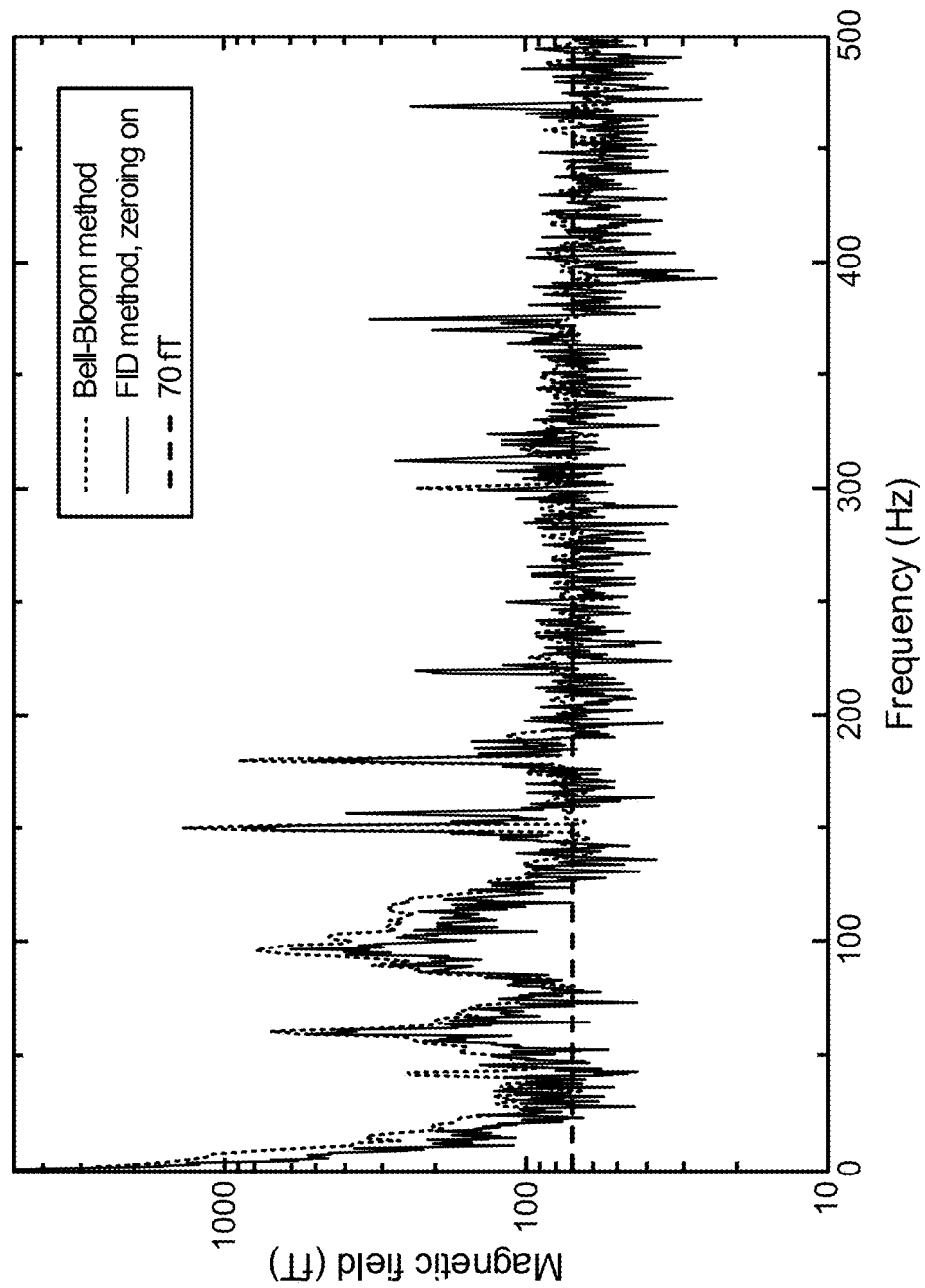
FIG. 15 shows an example of a comparison of magnetometer noise floor below 100 fT/Hz$^{1/2}$ using the Bell-Bloom and FID schemes in experiments performed with a 68 mm$^3$ glass-blown vapor cell.

FIG. 15 demonstrates the noise floor reached with the 68 $mm^3$ glass-blown vapor cell magnetometer using the Bell-Bloom and the FID schemes. Although the data analysis is completely different, the two methods of measuring the magnetometer's noise floor agree and demonstrate noise floors below 100 $fT/Hz^{1/2}$.

FID Method of Data Acquisition

Figure 16A:
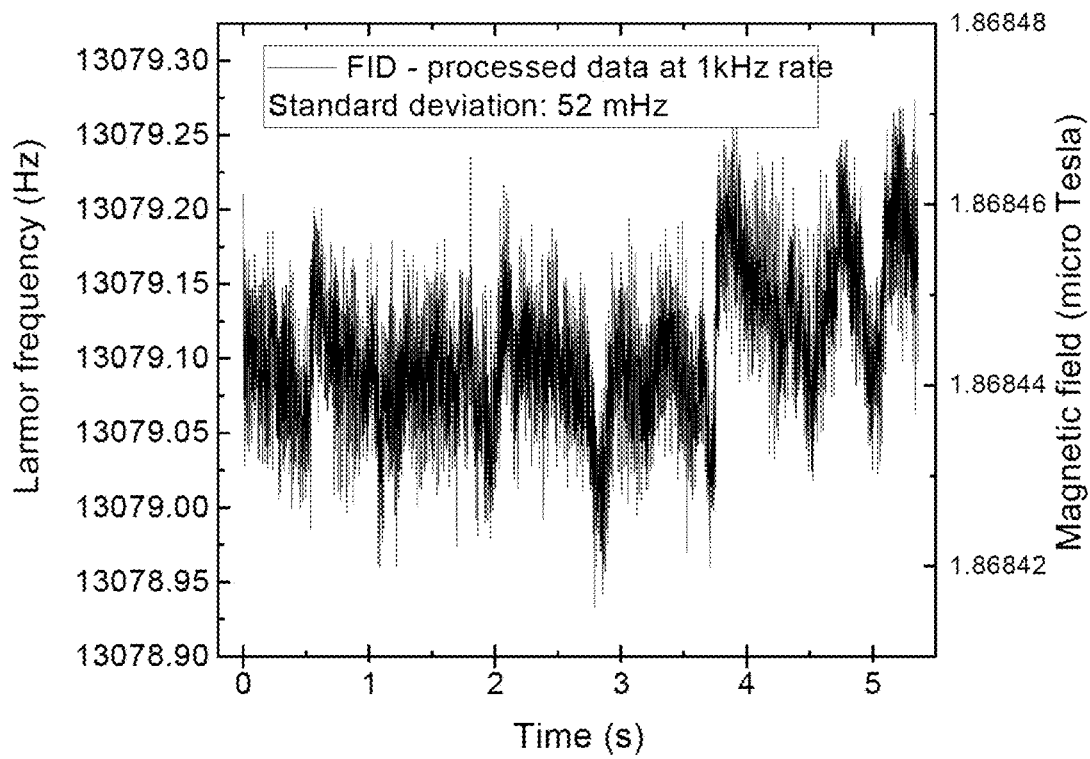
FIG. 16A shows a single 1 ms long FID measurement with the 68 mm$^3$ glass-blown vapor cell.

FIG. 16A shows a single 1 ms long FID measurement with the 68 $mm^3$ glass-blown vapor cell. The output shown is of the FID magnetometer over a single measurement cycle. The cycle lasts 1 ms and incorporates the pumping phase (not shown) and much longer detection phase. The data is analyzed off-line using nonlinear fit model to extract the FID frequency (around 13 kHz).

Figure 16B:
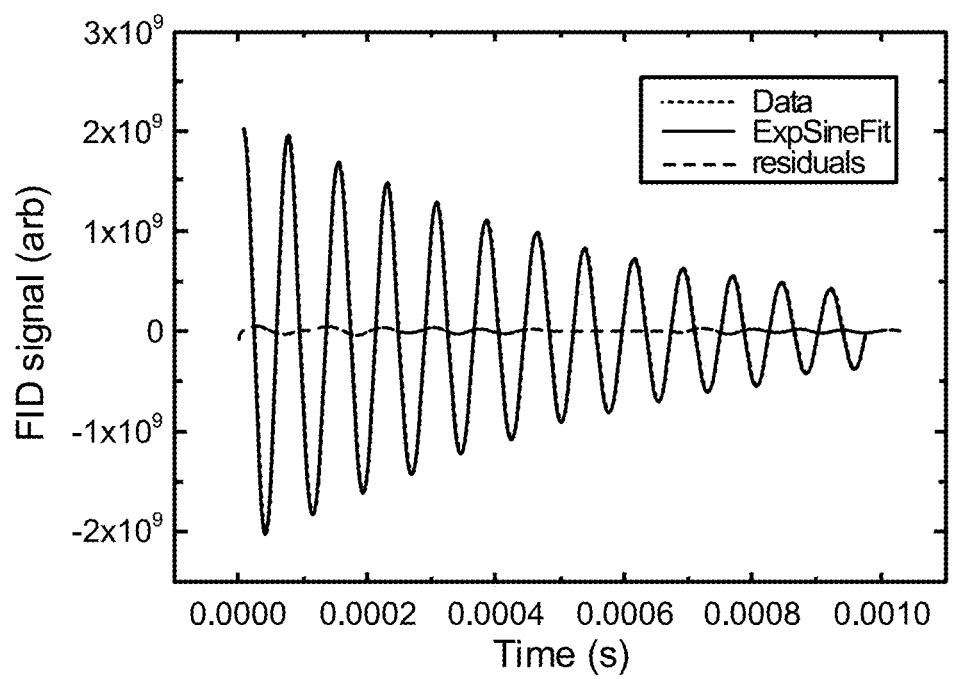
FIG. 16B shows FID frequency measurements repeated at a 1 kHz repetition rate with the 68 mm$^3$ glass-blown vapor cell.

FIG. 16B shows FID frequency measurements repeated at a 1 kHz repetition rate with the 68 $mm^3$ glass-blown vapor cell. The frequency data can be converted to magnetic field using the gyromagnetic ratio of $^{87}Rb$ of ~7 kHz/J. The spectrum of the frequency measurements is shown in FIG. 15, and is compared with the spectrum obtained with the Bell-Bloom method.

Increased-Bandwidth FID Magnetometer

The optically-pumped magnetometer bandwidth is typically limited to less than 1 kHz (our case). In certain medical applications (epilepsy, magnetic nanoparticle relaxometry), the limited bandwidth of the optically pumped magnetometers is an issue. Existing methods to increase the bandwidth are to broaden the magnetic resonance, or to use feedback from the atomic polarization precession to drive the spin synchronization.

Figure 17:
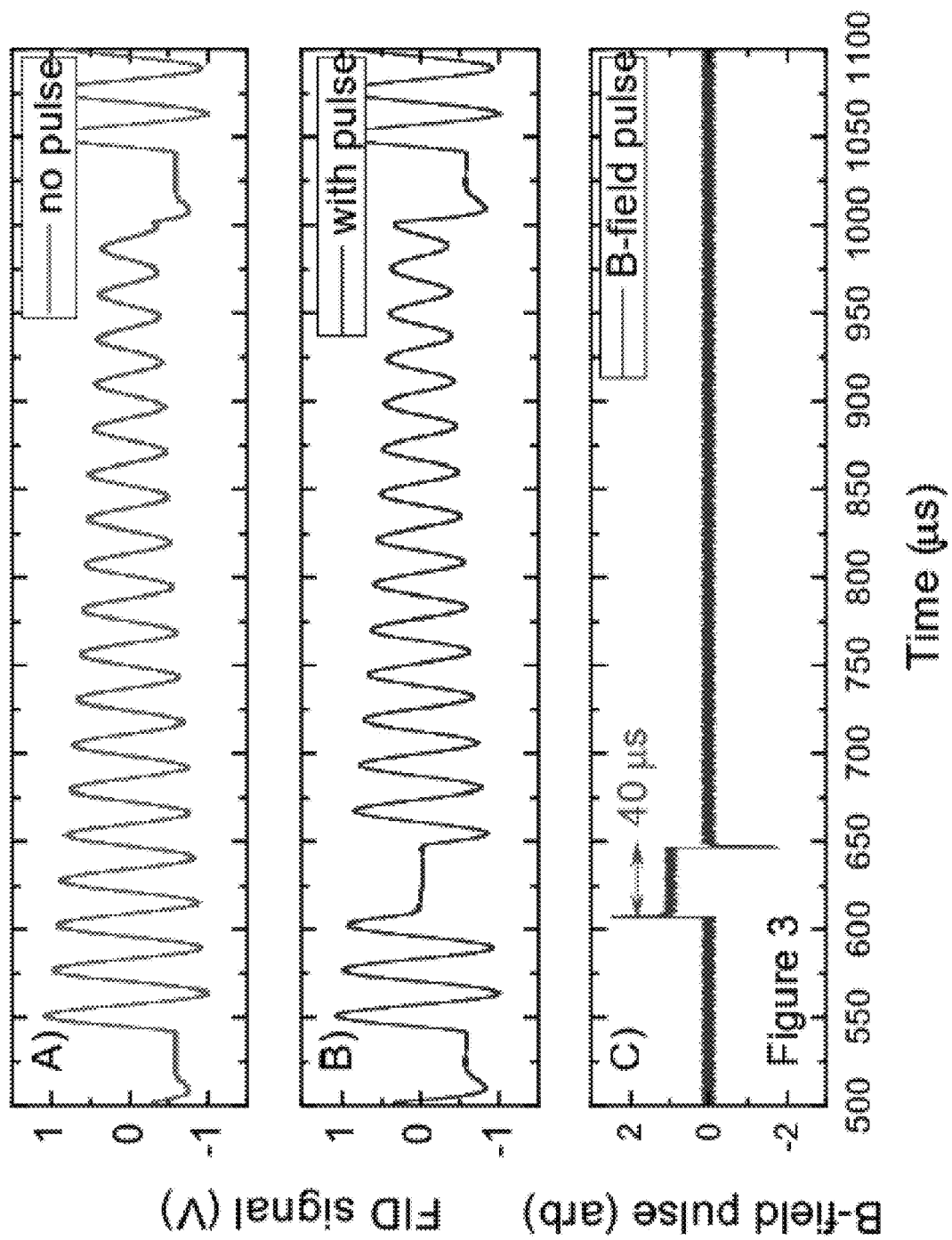
FIG. 17 illustrates examples of a typical FID signal (no magnetic field modulation) with the 18 mm$^3$ microfabricated cell (top panel), the FID signal with a magnetic field pulse applied during the detection phase with the 18 mm$^3$ microfabricated cell (middle panel), and the time dependence of the magnetic field pulse with the 18 mm$^3$ microfabricated cell (bottom panel).

In the FID method, the FID signal is acquired after the process of optical pumping is finished. The FID signal is the manifestation of the phase evolution of the atoms prepared in a coherent superposition. A typical FID signal is shown in the topmost plot of FIG. 17.

The phases of the atomic wave functions describing the internal atomic states changes instantaneously with changes of the total magnetic field. For example, if magnetic field pulses in opposite or the same direction as the bias magnetic field are applied after the atomic polarization precession has started, the precession can be stopped (see the middle plot of FIG. 17) or its frequency increased. The stepwise change of the total magnetic field (shown in the bottom plot of FIG. 17) acts instantaneously on the phase of the Larmor precession which is governed by the temporal evolution of the atomic wave functions, and is much faster than the typical 1 kHz bandwidth of the optically pumped magnetometer of the present technology, for which typically the optical pumping process is intrinsic part of the measurement cycle. In our measurement, the bandwidth of the field step measurement is limited by the bandwidth of the photodetector (100 kHz) and the rise time of the magnetic pulse is >25 kHz (rise time below 40 µs).

Analyzing FID signals, one can acquire information about magnetic field processes that are significantly faster than the magnetometer bandwidth of 1 kHz. Of course, one cannot realize the full magnetometer sensitivity in a single FID period, which is chosen comparable to the decoherence time $T_2$ (~0.5 ms in our case). But one can study periodic processes synchronous with the measurement cycle and still achieve the full magnetometer sensitivity by averaging multiple measurement cycles, while maintaining bandwidth to >25 kHz or higher.

Figure 18A:
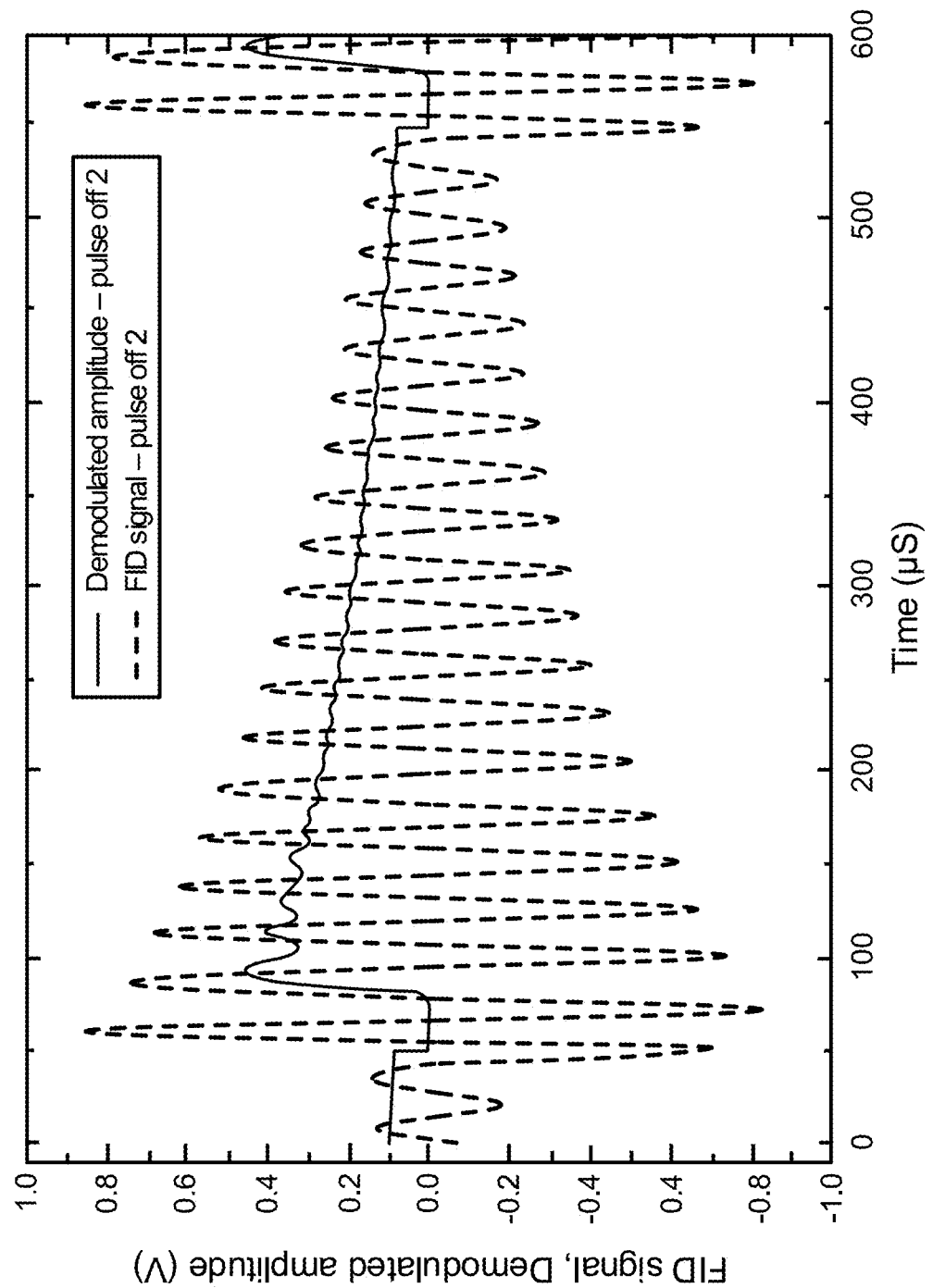
FIG. 18A-18D show examples of the FID signals without and with magnetic field modulation with the 18 mm$^3$ microfabricated cell.
Figure 18B:
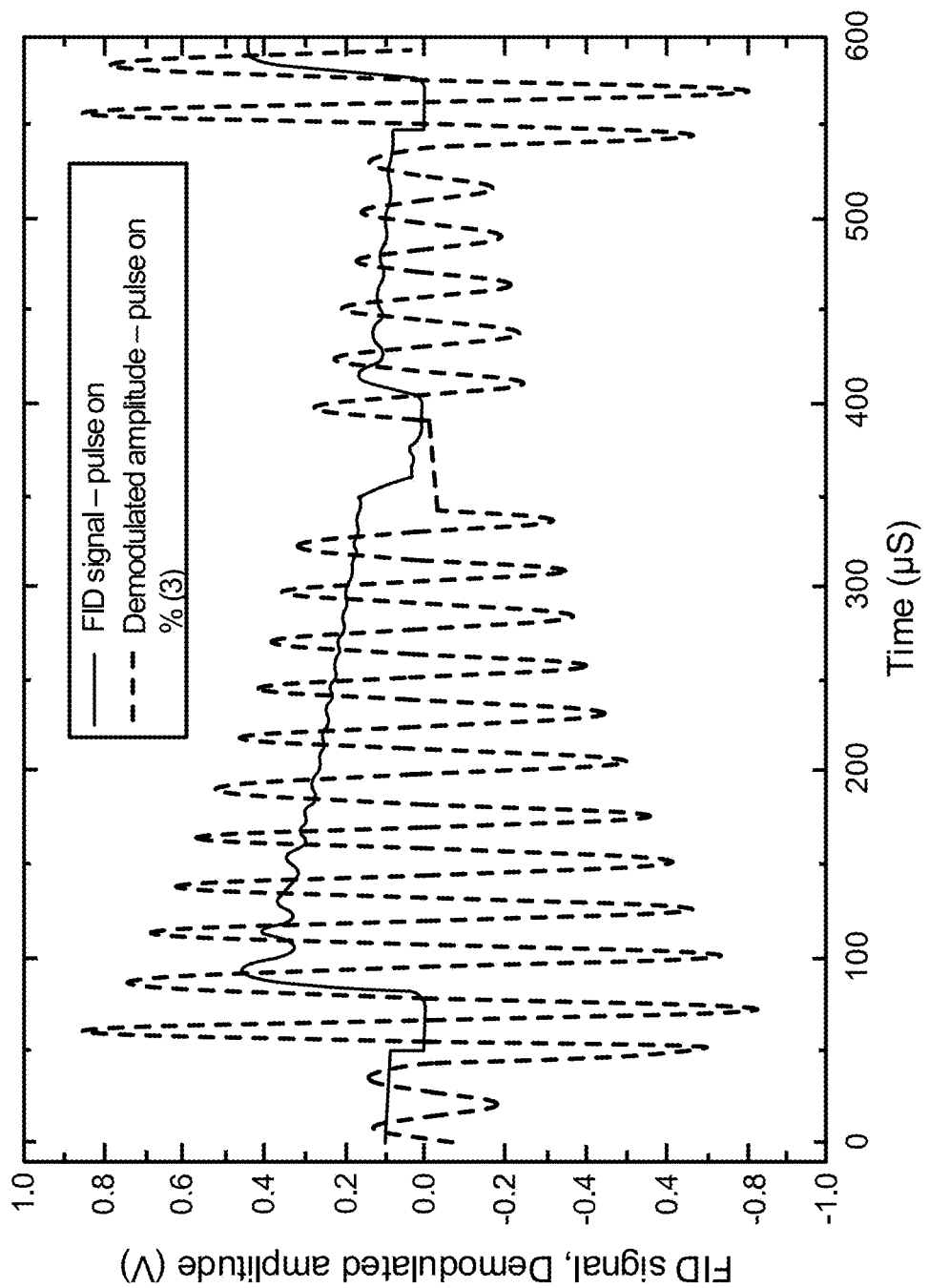
Figure 18C:
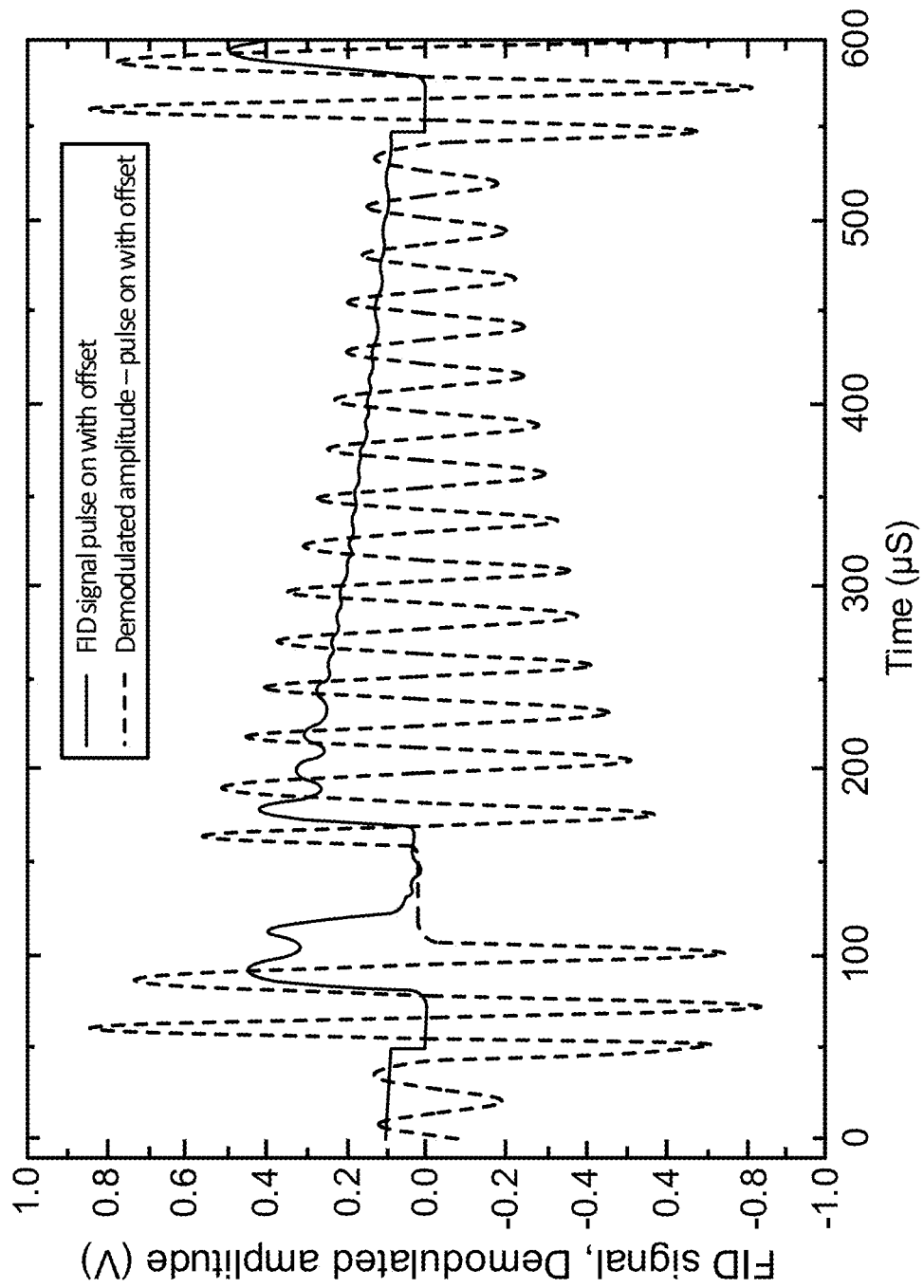
Figure 18D:
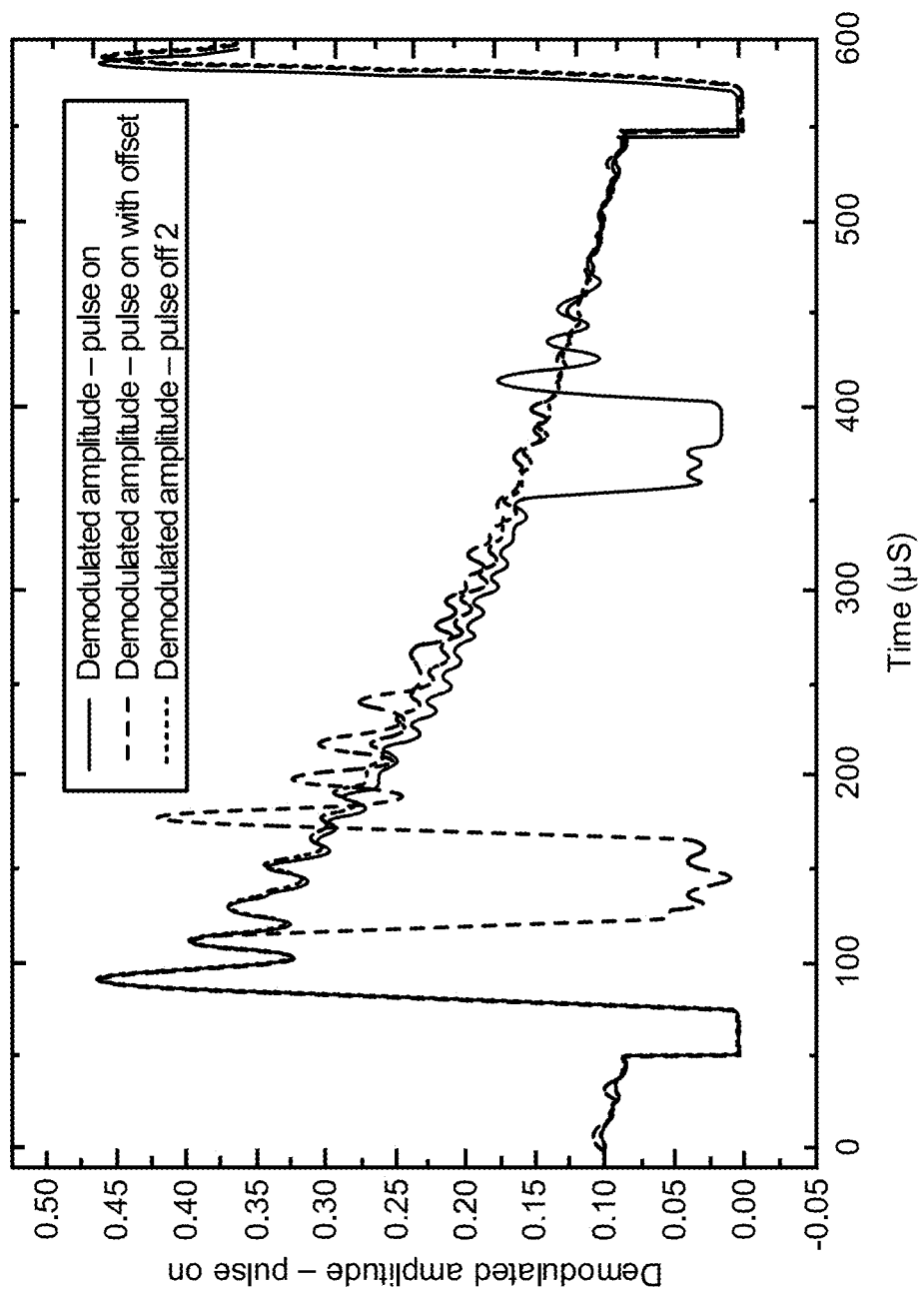

FIGS. 18A-18D shows the effect of applying a magnetic field modulation during the acquisition of the FID signal. FIG. 18A shows the FID signal without modulation. The dashed line trace is the FID magnetometer output; the solid line trace is the signal-processed signal amplitude. The offset between the dashed and solid line traces is due to the low-pass digital filter used for signal processing and is the same for all measurements. FIGS. 18B and 18C show the effect of 50 µs magnetic field pulse modulation applied at different times, with 237 µs time offset. During the 50 µs pulse, the effective magnetic field (and the Larmor precession frequency) at the sensor's position is close to zero. FIG. 18D compares the FID amplitudes in the cases shown in FIGS. 18A-18C after the signal processing.

Figure 19:
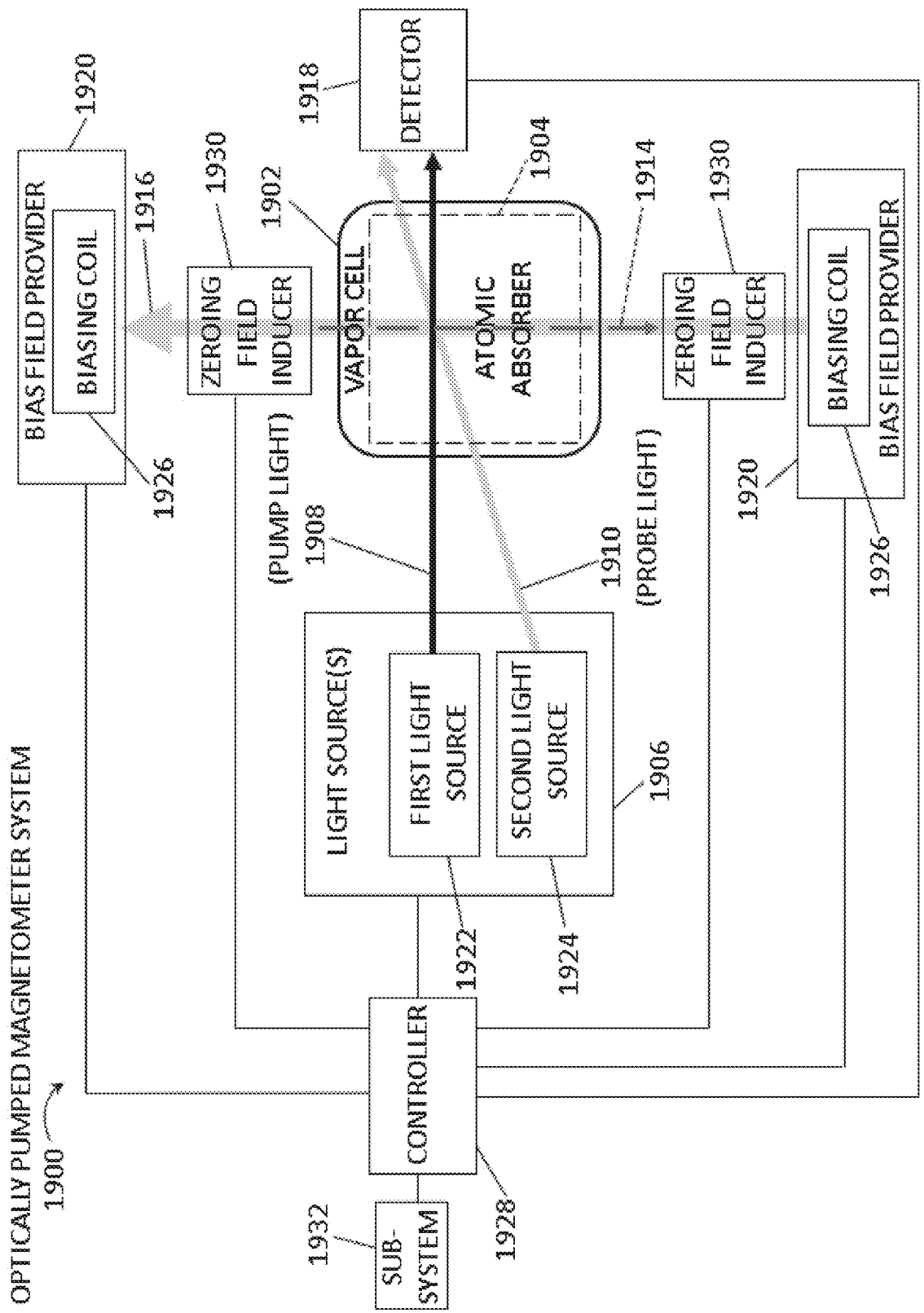
FIG. 19 shows a block diagram of an optically pumped magnetometer system.

FIG. 19 shows a block diagram of an optically pumped magnetometer system 1900 according to embodiments of the present technology. System 1900 may function in the same or similar way, and to the same or similar ends, as the above-described optically pumped magnetometer according to the present technology. Referring also to the foregoing figures and accompanying description, system 1900 includes a vapor cell 1902 for containing an atomic absorber 1904. The atomic absorber 1904 contained within the vapor cell 1902 may be, or include, $^{87}$Rb. Other suitable atomic absorbers may be utilized in system 1900. System 1900 includes at least one light source 1906. Light source(s) 1906 may be positioned and configured in system 1900 to be in optical communication with the vapor cell 1902. The at least one light source 1908 is configured to generate, and direct, a pump light (1908), and a probe light (1910), into and through the vapor cell 1902 along one or more light transmission path(s). In some embodiments, the at least one light source 1906 includes at least two light sources 1906. The at least two light sources 1906 can include a first light source 1922 to generate the pump light 1908, and a second light source 1924 to generate the probe light 1910.

The system 1900 includes means 1920 for providing, by inducing or otherwise, a bias field 1916 within the vapor cell 1902. In an example, the means 1920 for providing the bias field 1916 includes a device or mechanism (e.g., a swivel or similar adjustable mount) operatively coupled to at least the vapor cell 1902 of system 1900 to adjust a position of the vapor cell 1902 in three dimensional space in order to orient Earth's magnetic field (and/or another externally generated and applied magnetic field) to pass through an interior of the vapor cell 1902 at a desired orientation. In another example, the means 1920 for providing the bias field 1916 includes one or more biasing coils 1926 positioned sufficiently relative to the vapor cell 1902 to induce the bias field 1916 within the vapor cell 1902.

The system 1900 includes means 1930 for inducing, or otherwise providing, a zeroing field 1914 within the vapor cell 1902. In an example, the means 1920 for inducing the zeroing field 1914 may be positioned sufficiently relative to the vapor cell 1902 and/or relative to the means 1920, to zero the bias field 1920 upon inducing the zeroing field 1914.

In some embodiments, the system 1900 includes at least one detector 1918. The at least one detector 1918 may be positioned in the light transmission path of the at least one light source 1906. In the example shown in FIG. 19, the at least one light source 1906 is positioned adjacent to one end of the vapor cell 1902 and the detector 1918 is positioned adjacent to an opposite end of the vapor cell 1902 across from the light source(s) 1906. Detector(s) 1918 may be configured for use in system 1900 to directly or indirectly means a total magnetic field, or variations in the same, within the vapor cell 1902.

Some embodiments of system 1900 include a controller 1928 operatively coupled to at least one of: the at least light source 1906, the means 1920 for providing the bias field 1916, the means 1930 for inducing the zeroing field 1914, and the detector 1918. In one example, the controller 1928 is operatively coupled to the at least one light source 1906, and is configured to control a timing sequence of energizing the at least one light source 1906 to alternately provide the pump light 1908, and the probe light 1910, through the vapor cell 1902. In another example, the controller 1928 is operatively coupled to the means 1930 for inducing the zeroing field 1914, and is configured to control a timing sequence of energizing the means 1930 for inducing the zeroing field 1914 to alternately enable, and disable, the zeroing field 1914 within the vapor cell 1902. In yet another example, the controller 1928 is operatively coupled to the means 1920 for providing the bias field 1916, and is configured to control a timing sequence of the bias field 1916 being alternately enabled, and disabled, within the vapor cell 1902.

System 1900 may further include additional components or subsystems 1932 in addition to those described above. In one embodiment, a computer system with processor(s) and input/output devices like keyboards, monitors, a printer, and a mouse may be coupled in communication with controller 1928 and/or other system 1900 component parts. In such embodiments, the computer processors may execute software, or similarly direct the controller 1928 to execute firmware, to facilitate performance of one or more of the steps of the methods for operating an optically pumped magnetometer according to the present technology. This may include data analysis operations, control operations, component configuration (e.g., of detector 1918, light source(s) 1906, and/or means 1920 and/or 1930), data visualization, data storage, and the like to facilitate a human operator to perform such methods as described by way of example herein.

Figure 20:
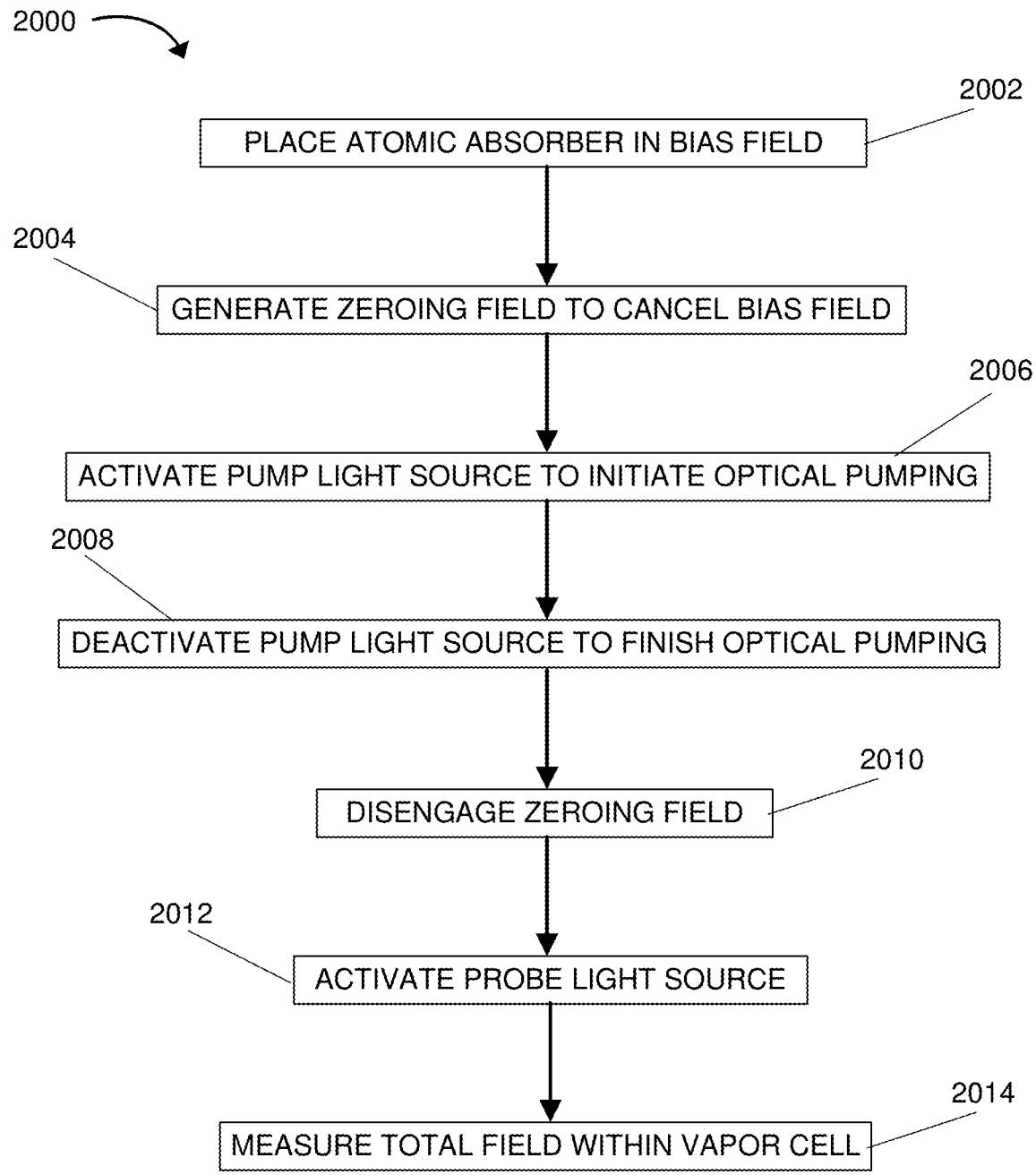
FIG. 20 shows a flow chart of a method for operating an optically pumped magnetometer.

FIG. 20 shows a flow chart of a method 2000 for operating an optically pumped magnetometer according to embodiments of the present technology. Referring also to the foregoing figures and accompanying description, method 2000 includes the step of placing 2002 an atomic absorber in a bias field within a vapor cell of an optically pumped magnetometer. The atomic absorber contained within the vapor cell during performance of method 2000 may be, or include, $^{87}$Rb. Other suitable atomic absorbers may be utilized in method 2000. Method 2000 also includes the step of generating 2004 a zeroing field to cancel the bias field within the vapor cell of the optically pumped magnetometer.

Method 2000 can also include the step of activating 2006 a pump light source of the optically pumped magnetometer to initiate optical pumping within the vapor cell. Method 2000 can further include the step of deactivating 2008 the pump light source of the optically pumped magnetometer to finish the optical pumping in the vapor cell. Method 2000 may also include the step of disengaging 2010 the zeroing field within the vapor cell of the optically pumped magnetometer. Method 2000 may further include the step of activating 2012 a probe light source of the optically pumped magnetometer. Method 2000 can also include the step of measuring 2014 the total field within the vapor cell.

The method 2000 step of activating 2012 the probe light source may include activating the probe light source during the optical pumping. In an embodiment, the method 2000 step of generating 2004 the zeroing field may include activating zeroing coils to zero the bias field. In another embodiment, the step of generating 2004 the zeroing field may include applying the zeroing field in a direction opposite of that of the bias field.

In one embodiment, the method 2000 steps of activating 2006 the pump light source and activating 2012 the probe light source may include separately activating the pump and probe light sources from a single light source. In this embodiment of method 2000, the step of separately activating the pump and probe light sources from the single light source may include modifying at least one of: an amplitude, a frequency modification, and a modification to a state of polarization, of the single light source.

In some embodiments, method 2000 may include the step of turning off the pump light source using amplitude attenuation, frequency detuning, or by a change in a state of polarization. In other embodiments, method 2000 can include the step of detecting probe light polarization to detect the phase evolution of an atomic polarization of the atomic absorber caused by changes in the bias field.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited in particular claim formats, other aspects may likewise be embodied in the presented formats, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A system comprising:
   a vapor cell for containing an atomic absorber;
   at least one light source to:
   generate a pump light through the vapor cell; and
   generate a probe light through the vapor cell; and
   zeroing coils to zero a bias field within the vapor cell.

2. The system of claim 1, further comprising a detector for measuring a total field within the vapor cell.

3. The system of claim 1, wherein the atomic absorber includes rubidium-87.

4. The system of claim 1, further comprising means for providing the bias field within the vapor cell.

5. The system of claim 1, wherein the at least one light source includes at least two light sources including:
   a first light source to generate the pump light; and
   a second light source to generate the probe light.

6. The system of claim 1, further comprising biasing coils to induce the bias field within the vapor cell.

7. A method comprising:
   placing an atomic absorber in a bias field within a vapor cell of an optically pumped magnetometer;
   generating a zeroing field to cancel the bias field within the vapor cell of the optically pumped magnetometer;
   activating a pump light source of the optically pumped magnetometer to initiate optical pumping;
   deactivating the pump light source of the optically pumped magnetometer to finish the optical pumping;
   disengaging the zeroing field within the vapor cell of the optically pumped magnetometer;
   activating a probe light source of the optically pumped magnetometer; and
   measuring a total field within the vapor cell.

8. The method of claim 1, wherein generating the zeroing field includes activating zeroing coils to zero the bias field.

9. The method of claim 1, wherein generating the zeroing field comprises applying the zeroing field in a direction opposite of that of the bias field.

10. The method of claim 1, further comprising turning off the pump light source using amplitude attenuation, frequency detuning, or by a change in a state of polarization.

11. The method of claim 1, wherein activating the pump light source and activating the probe light source comprise separately activating the pump and probe light sources from a single light source.

12. The method of claim 11, wherein separately activating the pump and probe light sources from the single light source comprises modifying at least one of: an amplitude, a frequency modification, and a modification to a state of polarization, of the single light source.

13. The method of claim 1, further comprising detecting probe light polarization to detect a phase evolution of an atomic polarization of the atomic absorber caused by changes in the bias field.

14. The method of claim 1, wherein activating the probe light source comprises activating the probe light source during the optical pumping.

15. The method of claim 1, wherein the atomic absorber includes rubidium-87.

16. An optically pumped magnetometer, comprising:
   a vapor cell configured to contain an atomic absorber;
   at least one light source in optical communication with the vapor cell;
   means for providing a bias field within the vapor cell; and
   means for inducing a zeroing field within the vapor cell positioned sufficiently relative to the vapor cell to zero the bias field upon inducing the zeroing field.

17. The optically pumped magnetometer of claim 16, further comprising a controller operatively coupled to at least one of: the at least light source, the means for providing the bias field, and the means for inducing the zeroing field.

18. The optically pumped magnetometer of claim 17, wherein the controller is operatively coupled to the at least one light source, and is configured to control a timing sequence of energizing the at least one light source to alternately provide a pump light, and a probe light, through the vapor cell.

19. The optically pumped magnetometer of claim 17, wherein the controller is operatively coupled to the means for inducing the zeroing field, and is configured to control a timing sequence of energizing the means for inducing the zeroing field to alternately enable, and disable, the zeroing field within the vapor cell.

20. The optically pumped magnetometer of claim 16, wherein the at least one light source is configured to direct a pump light, and a probe light, into the vapor cell along a path.

* * * * *